(12) United States Patent
Haseba et al.

(10) Patent No.: US 6,326,065 B1
(45) Date of Patent: *Dec. 4, 2001

(54) PYRIMIDINE DERIVATIVE, LIQUID CRYSTAL COMPOSITION COMPRISING THE DERIVATIVE, AND LIQUID CRYSTAL DISPLAY DEVICE FABRICATED BY USING THE COMPOSITION

(75) Inventors: Yasuhiro Haseba; Shuichi Matsui; Kazutoshi Miyazawa; Hiroyuki Takeuchi; Yoshitaka Tomi; Fusayuki Takeshita; Etsuo Nakagawa, all of Chiba (JP)

(73) Assignee: Chisso Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/203,671

(22) Filed: Dec. 1, 1998

(51) Int. Cl.[7] .......................... C09K 19/30; C09K 19/34; C09K 19/20; C07D 239/02
(52) U.S. Cl. .............. 428/1.1; 252/299.01; 252/299.61; 252/299.63; 252/299.64; 252/299.65; 252/299.66; 252/299.67; 544/298; 544/334; 544/335
(58) Field of Search .................. 252/299.01, 299.61, 252/299.63, 299.64, 299.65, 299.66, 299.67; 428/1.1; 544/298, 334, 335

(56) References Cited

U.S. PATENT DOCUMENTS

| | | | |
|---|---|---|---|
| 5,454,975 | * 10/1995 | Reiffenrath et al. | 252/299.61 |
| 5,482,650 | * 1/1996 | Janulis et al. | 252/299.01 |
| 5,562,858 | * 10/1996 | Bartmann et al. | 252/299.66 |
| 5,580,488 | * 12/1996 | Nakamura et al. | 252/299.61 |
| 5,709,818 | * 1/1998 | Yamashita et al. | 252/299.61 |

FOREIGN PATENT DOCUMENTS 7-101894 * 4/1995 (JP).
98/23561 * 6/1998 (WO).

* cited by examiner

Primary Examiner—Shean C. Wu
(74) Attorney, Agent, or Firm—Wenderoth, Lind & Ponack, L.L.P.

(57) ABSTRACT

Liquid crystalline compounds having a comparatively high voltage holding ratio, high $\Delta n$ and high $\Delta\epsilon$, and excellent miscibility with known liquid crystalline compounds at low temperatures. The novel compounds have the formula (1)

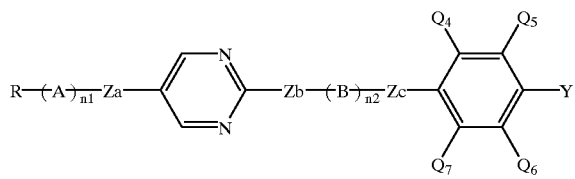

(1)

wherein R represents hydrogen atom or an alkyl group having 1 to 20 carbon atoms; n1 and n2 are independently 0, 1, or 2 provided that the sum of n1 and n2 is 1 or 2; ring A and ring B independently represent 1,4-phenylene, fluorine substituted 1,4-phenylene expressed by the formula (a) in the specification or 1,4-cyclohexylene provided that at least one of ring A and ring B is fluorine substituted 1,4-phenylene expressed by the formula (a); Za, Zb, and Zc independently represent single bond, —$CH_2CH_2$—, —COO—, —$CF_2O$—, or —$CH_2CH_2CH_2CH_2$—; $Q_1$, $Q_2$, $Q_3$, $Q_4$, $Q_5$, $Q_6$, and $Q_7$ independently represent hydrogen atom, a halogen atom, or methyl group provided that when at least one of Za, Zb, and Zc is —$CH_2CH_2$—, then $Q_2$ is fluorine atom, and that when Za, Zb, and Zc are all single bonds, then $Q_1$, $Q_2$, $Q_3$, $Q_4$, $Q_5$, $Q_6$, and $Q_7$ independently represent hydrogen atom or fluorine atom; Y represents hydrogen atom, a halogen atom, or a halogenated alkyl group having 1 to 5 carbon atoms; and each atom constituting this compound may be replaced by its isotope.

32 Claims, No Drawings

PYRIMIDINE DERIVATIVE, LIQUID CRYSTAL COMPOSITION COMPRISING THE DERIVATIVE, AND LIQUID CRYSTAL DISPLAY DEVICE FABRICATED BY USING THE COMPOSITION

TECHNICAL FIELD

The present invention relates to novel liquid crystalline compounds (hereinafter, the term "liquid crystalline compound" is used as a general name for compounds having liquid crystal phase and compounds which do not exhibit liquid crystal phase but are useful as component of liquid crystal compositions). Specifically, the invention relates to liquid crystalline compounds which are preferable for using as component of liquid crystal compositions for TFT type liquid crystal display devices; relates to liquid crystal compositions comprising the liquid crystalline compound; and relates to liquid crystal display devices fabricated by using the liquid crystal composition.

BACKGROUND ART

Liquid crystal display devices employ optical anisotropy and dielectric anisotropy of liquid crystal substances, and display mode of the devices includes TN (twisted nematic) mode, DS (dynamic scattering) mode, G.H (guest.host) mode, DAP (deformation of aligned phases) mode, and STN (super twisted nematic) mode. In order to cope with the request for higher display quality, the demand for display devices of active matrix type a typical example of which is thin film transistor (TFT) has recently been increased.

While properties required of liquid crystal substances are different from the mode to mode, liquid crystal substances are necessary to be stable against moisture, air, heat, and light in any display mode. Besides, the substances should exhibit liquid crystal phase in a temperature range as wide as possible with room temperature being its center, should have a low viscosity, excellent miscibility with other liquid crystalline compounds, large dielectric anisotropy value ($\Delta\epsilon$), and most desirable optical anisotropy value ($\Delta n$), and should be chemically and electrically stable. Particularly, a high voltage holding ratio is required of display devices of active matrix type. However, compounds which completely satisfy such requirements as mentioned above by a single compound have not been found up to now, and thus it is an actual situation that liquid crystal compositions obtained by mixing several kind of liquid crystal compounds or liquid crystalline compounds are being used.

Recently, liquid crystal display devices which can be driven at a low voltage and have a high response speed are sought for TFT type liquid crystal devices. Accordingly, development of liquid crystal materials exhibiting a high voltage holding ratio, and having a high $\Delta n$ and high $\Delta\epsilon$ is actively being carried out.

Heretofore, it is known that fluorine substituted liquid crystal materials exhibit a high voltage holding ratio, and that liquid crystalline compounds having a plural number of aromatic rings have a high $\Delta n$. It is also known that compounds in which aromatic ring is pyrimidine ring have a high $\Delta\epsilon$. Based on these knowledge, it can be expected that liquid crystalline compounds which have pyrimidine ring and fluorinated phenyl ring have a high $\Delta n$ and a high $\Delta\epsilon$, and are also high in voltage holding ratio. In Laid-open Japanese Patent Publication No. Hei 2-233626, a liquid crystalline compound (compound expressed by the formula 10) having pyrimidine ring and partially being replaced by fluorine atom is disclosed.

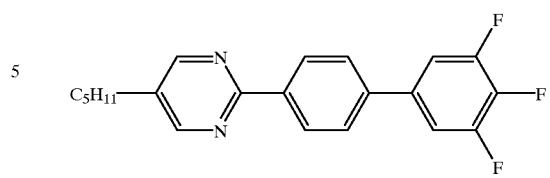

(10)

Voltage holding ratio of the compound (formula 10) was 97.5% at 25° C. and 92.9% at 100° C., synthesis and determination of voltage holding ratio of which were carried out by the present inventors according to the description in Laid-open Japanese Patent Publication No. Hei 2-233626. Besides, physical properties of the compound (formula 10) which was calculated by extrapolation from physical properties both of (a) the composition obtained by dissolving the compound (formula 10) in a mother liquid crystal having nematic phase and (b) the mother liquid crystal itself, and their mixing ratio were as follows:

| N-I transition point | 83.7° C. |
|---|---|
| $\Delta\epsilon$ | 18.7 |
| $\Delta n$ | 0.204 |

Whereas this compound has a comparatively high voltage holding ratio, its $\Delta\epsilon$ value is insufficient for coping with the request for driving liquid crystal display devices at a low voltage. Besides, the compound (formula 10) has a defect, as shown in Comparative Examples described below, that miscibility with other liquid crystalline compounds at low temperatures is poor. Since the mixing ratio of liquid crystal compounds having a poor miscibility at low temperature in liquid crystal compositions can not be increased, it is impossible to make the characteristics of such compounds contribute to the improvement of characteristics of liquid crystal compositions even if the compounds had some other excellent characteristics.

An object of the present invention is to provide liquid crystalline compounds which have a high voltage holding ratio, high $\Delta n$, and high $\Delta\epsilon$, and are excellent in miscibility with other liquid crystalline compounds at low temperatures; to provide liquid crystal compositions comprising the liquid crystalline compound; and to provide liquid crystal display devices fabricated by using the liquid crystal composition.

DISCLOSURE OF THE INVENTION

As a result of diligent investigation by the present inventors, it has been found out that compounds having 1,4-phenylene group at least one hydrogen atom of which is replaced by fluorine atom at a lateral position, and pyrimidine-2,5-diyl group, and being expressed by the general formula (1) have expected properties as liquid crystalline compounds, leading to the achievement of the present invention. That is, the present invention is summarized as follows:

(1) A pyrimidine derivative expressed by the general formula (1)

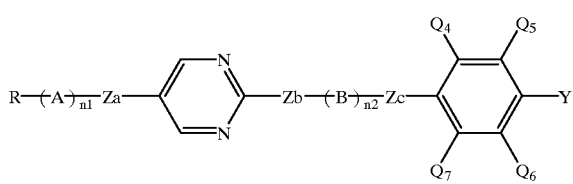

(1)

wherein R represents hydrogen atom or an alkyl group having 1 to 20 carbon atoms, at least one hydrogen atom in the alkyl group may be replaced by a halogen atom, and at least one —$CH_2$— in the alkyl group may be replaced by oxygen atom or —CH=CH— but in no case oxygen atoms adjoin to each other;

n1 and n2 are independently 0, 1, or 2 provided that the sum of n1 and n2 is 1 or 2;

ring A and ring B independently represent 1,4-phenylene, fluorine substituted 1,4-phenylene expressed by the formula (a)

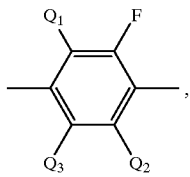

(a)

or 1,4-cyclohexylene provided that at least one of ring A and ring B is fluorine substituted 1,4-phenylene expressed by the formula (a), and that when ring A and/or ring B is the fluorine substituted 1,4-phenylene, n1 and/or n2 is 1 or 2, at least one not-adjacent —$CH_2$— in the 1,4-cyclohexylene may be replaced by oxygen atom, and at least one hydrogen atom in the 1,4-cyclohexylene may be replaced by a halogen atom;

Za, Zb, and Zc independently represent single bond, —$CH_2CH_2$—, —COO—, —$CF_2O$—, or —$CH_2CH_2CH_2CH_2$—;

$Q_1$, $Q_2$, $Q_3$, $Q_4$, $Q_5$, $Q_6$, and $Q_7$ independently represent hydrogen atom, a halogen atom, or methyl group provided that when at least one of Za, Zb, and Zc is —$CH_2CH_2$—, $Q_2$ is fluorine atom;

Y represents hydrogen atom, a halogen atom, or a halogenated alkyl group having 1 to 5 carbon atoms, at least one not-adjacent methylene group in the halogenated alkyl group may be replaced by oxygen atom or sulfur atom; and each atom constituting this compound may be replaced by its isotope.

(2) The pyrimidine derivative recited in paragraph (1) above wherein n1 is 0, n2 is 1, all of Za, Zb, and Zc are single bond, both of $Q_1$ and $Q_3$ are hydrogen atom, and $Q_2$ is fluorine atom in the general formula (1).

(3) The pyrimidine derivative recited in paragraph (1) above wherein n1 is 0, n2 is 1, all of Za, Zb, and Zc are single bond, and all of $Q_1$, $Q_2$, and $Q_3$ are hydrogen atom in the general formula (1).

(4) The pyrimidine derivative recited in paragraph (1) above wherein n1 is 1 and n2 is 0 in the general formula (1).

(5) The pyrimidine derivative recited in paragraph (1) above wherein n1 is 0, n2 is 1, both Za and Zb are single bond, and Zc is —COO— or —$CF_2O$— in the general formula (1).

(6) The pyrimidine derivative recited in paragraph (1) above wherein n1 is 0, n2 is 1, both Za and Zc are single bond, and Zb is —COO— or —$CF_2O$— in the general formula (1)

(7) The pyrimidine derivative recited in paragraph (1) above wherein n1+n2=2 in the general formula (1).

(8) The pyrimidine derivative recited in paragraph (1) above wherein R is an alkyl group at least one hydrogen atom in which is replaced by fluorine atom in the general formula (1).

(9) A liquid crystal composition comprising at least one pyrimidine derivative recited in any one of paragraphs (1) to (8) above.

(10) A liquid crystal composition comprising, as a first component, at least one pyrimidine derivative recited in any one of paragraphs (1) to (8) above, and comprising, as a second component, at least one compound selected from the group consisting of the compounds expressed by the general formula (2), (3), or (4)

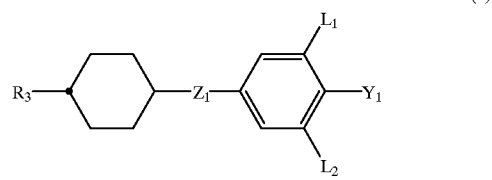

(2)

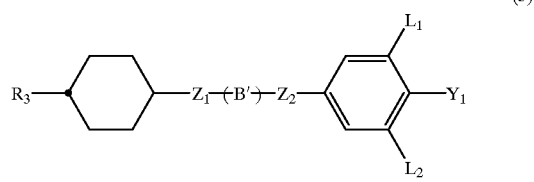

(3)

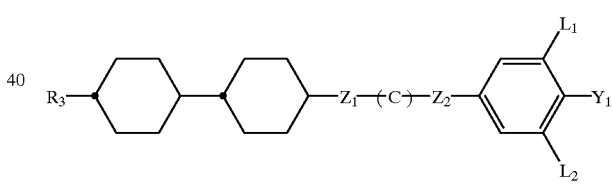

(4)

wherein $R_3$, $Y_1$, $L_1$, $L_2$, $Z_1$, and $Z_2$ may be the same or different among the formulas, $R_3$ represents an alkyl group having 1 to 10 carbon atoms, at least one not-adjacent methylene group in the alkyl group may be replaced by oxygen atom or —CH=CH—, and any hydrogen atom in the alkyl group may be replaced by fluorine atom; Yi represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$; $L_1$ and $L_2$ independently represent hydrogen atom or fluorine atom; Z, and $Z_2$ independently represent —$CH_2CH_2$—, —$CH_2CH_2CH_2CH_2$—, —COO—, —$CF_2O$—, —$OCF_2$—, —CH=CH—, or single bond; ring B' represents trans-1,4-cyclohexylene, 1,3-dioxane-2,5-diyl, or 1,4-phenylene hydrogen atom of which may be replaced by fluorine atom; ring C represents trans-1,4-cyclohexylene or 1,4-phenylene hydrogen atom of which may be replaced by fluorine atom; and each atom constituting this compound may be replaced by its isotope.

(11) A liquid crystal composition comprising, as a first component, at least one pyrimidine derivative recited in any one of paragraphs (1) to (8) above, and comprising, as a second component, at least one compound selected from the group consisting of the compounds expressed by the general formula (5) or (6)

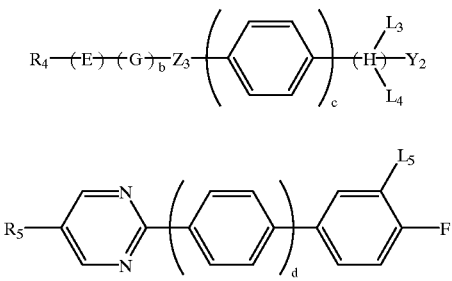

wherein $R_4$ and $R_5$ independently represent an alkyl group having 1 to 10 carbon atoms, at least one not-adjacent methylene group in the alkyl group may be replaced by oxygen atom or —CH=CH—, and hydrogen atom in the alkyl group may be replaced by fluorine atom; $Y_2$ represents —CN or —C≡C—CN; ring E represents trans-1,4-cyclohexylene, 1,4-phenylene, 1,3-dioxane-2,5-diyl, or pyrimidine-2,5-diyl; ring G represents trans-1,4-cyclohexylene, pyrimidine-2,5-diyl, or 1,4-phenylene hydrogen atom of which may be replaced by fluorine atom; ring H represents trans-1,4-cyclohexylene or 1,4-phenylene, $Z_3$ represents —CH$_2$CH$_2$—, —COO—, or single bond; $L_3$, $L_4$, and $L_5$ independently represent hydrogen atom or fluorine atom; b, c, and d are independently 0 or 1; and each atom constituting this compound may be replaced by its isotope.

(12) A liquid crystal composition comprising, as a first component, at least one pyrimidine derivative defined in any one of paragraphs (1) to (8) above, comprising, as a second component, at least one compound selected from the group consisting of the compounds expressed by the general formula (2), (3), or (4) recited in paragraph (10) above, and comprising, as a third component, at least one compound selected from the group consisting of the compounds expressed by the general formula (7), (8), or (9)

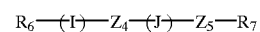

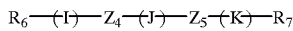

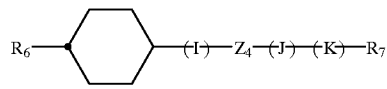

wherein $R_6$, $R_7$, I, J, and K may be the same or different among the general formulas, $R_6$ and $R_7$ independently represent an alkyl group having 1 to 10 carbon atoms, at least one methylene group in the alkyl group may be replaced by oxygen atom or —CH=CH—, and any hydrogen atom in the alkyl group may be replaced by fluorine atom; ring I, ring J, and ring K independently represent trans-1,4-cyclohexylene, pyrimidine-2,5-diyl, or 1,4-phenylene hydrogen atom of which may be replaced by fluorine atom; $Z_4$ and $Z_5$ independently represent —C≡C—, —COO—, —CH$_2$CH$_2$—, —CH=CH—, or single bond; and each atom constituting this compound may be replaced by its isotope.

(13) A liquid crystal composition comprising, as a first component, at least one pyrimidine derivative recited in any one of paragraphs (1) to (8) above, comprising, as a second component, at least one compound selected from the group consisting of the compounds expressed by the general formula (5) or (6) recited in paragraph (11) above, and comprising, as a third compound, at least one compound selected from the group consisting of the compounds expressed by the general formula (7), (8), or (9) recited in paragraph (12) above. (14) A liquid crystal composition comprising, as a first component, at least one pyrimidine derivative recited in paragraphs (1) to (8) above, comprising, as a part of a second component, at least one compound selected from the group consisting of the compounds expressed by the general formula (2), (3), or (4) recited in paragraph (10) above, comprising, as another part of the second component, at least one compound selected from the group consisting of the compounds expressed by the general formula (5) or (6) recited in paragraph (11) above, and comprising, as a third component, at least one compound selected from the group consisting of the compounds expressed by the general formula (7), (8), or (9) recited in paragraph (12) above.

(15) A liquid crystal composition comprising the liquid crystal composition recited in any one of paragraphs (9) to (14) above and further comprising at least one optically active compound.

(16) A liquid crystal display device fabricated by using the liquid crystal composition recited in any one of paragraphs (9) to (15) above.

BEST MODE FOR CARRYING OUT THE INVENTION

Molecular terminal of the compounds of the present invention expressed by the general formula (1) is phenylene group at least one hydrogen atom of which may be replaced by a halogen-containing electron withdrawing groups. The compounds have at least one 1,4-phenylene group at least one hydrogen atom of which is replaced by fluorine atom, in addition to the phenylene group described just above and pyrimidine group. Thus, the compounds expressed by the general formula (1) are liquid crystalline compounds having three or four aromatic rings including pyrimidine ring. Based on such structure, the compounds have a comparatively high voltage holding ratio, high Δn, and high Δε, and are excellent in miscibility with other liquid crystalline compounds at low temperatures.

For instance, whereas compound (Compound No. 17) included in the scope of the present invention has the same alkyl chain as compound (of formula 10), the former compound has such a remarkably high Δε and has an excellent miscibility at low temperatures as described below. That is, physical properties of compound (of formula 10) are mentioned above. Then, it is surprising that Δε of compound (Compound No. 17) is 31.0 despite the fact that its N-I transition point is 48.4° C. as shown in Example 2.

As shown in Examples 6 and 7, whereas the concentration of a compound at which crystals are not separated when the compound is dissolved in a liquid crystal composition comprising a known fluorine substituted liquid crystalline compound and left at −20° C. for 30 days was lower than 5% with compound of the formula 10, the concentration was higher than 15% with compound (Compound No. 17) from which it can be seen that the compounds of the present invention have an excellent miscibility at low temperatures.

As shown in Examples 4 and 5, voltage holding ratio of compound (of formula 10) is 97.5% at 25° C. and 92.9% at 100° C., and compound (Compound No. 17) exhibits about the same values of 97.5% at 25° C. and 93.2% at 100° C.

Some of the compounds expressed by the general formula (1) are formally included in the scope of claims of WO 94/26840, DE 4,445,224, or Laid-open WO Japanese Patent Publication (Tokuhyo) Hei 4-503818. However, specific descriptions and data showing physical properties of the compounds of the present invention can not be found in these patent publications. Further, no descriptions which foresee such excellent characteristics of the compounds of the present invention as described above are included in the publications.

Now, the compounds of the present invention are described in more detail. Whereas the compounds in which one or more atoms constituting the compounds are replaced by their isotope are not described in the following, such compounds also have the same or similar characteristics as those of the compounds described below.

In general formula (1), R represents hydrogen atom or an alkyl, alkenyl, alkoxy, or alkoxyalkyl group having 1 to 20 carbon atoms, at least one hydrogen atom in the groups may be replaced by a halogen atom. However, these groups have preferably 1 to 7 and more desirably 2 to 5 carbon atoms from the viewpoint of the balance between low viscosity and high N-I transition point.

Whereas the compounds in which R is an alkyl group are excellent in the balance between viscosity and N-I transition point compared with the compounds in which R is a halogen substituted alkyl group, the latter compounds are excellent in miscibility with other liquid crystalline compounds at low temperatures. In the compounds in which R is a halogen substituted alkyl group, compounds in which one fluorine atom substituted terminal carbon atom are excellent in the balance between viscosity and N-I transition point.

Compounds in which R is an alkoxy group or alkoxyalkyl group exhibit an excellent miscibility at low temperatures. Compounds in which R is an alkenyl group are excellent in the balance between viscosity and N-I transition point, but poor in voltage holding ratio compared with the compounds in which R is an alkyl group.

In the general formula (1), n1 and n2 are independently 0, 1, or 2, and the sum of n1 and n2 is 1 or 2. Compounds in which the sum of n1 and n2 is 1 have a low viscosity, and the compounds in which the sum of n1 and n2 is 2 have a high N-I transition point.

Bonding group Za, Zb, and Zc independently represent single bond, —COO—, —CH$_2$CH$_2$—, —CH$_2$CH$_2$CH$_2$CH$_2$—, or —CF$_2$O—, and their features are described as follows:

Compounds in which all bonding groups Za, Zb, and Zc are single bond have a comparatively high N-I transition point, have a low viscosity, are excellent in miscibility with other liquid crystal compounds, and are chemically and electrically stable. Compounds in which at least one of bonding groups Za, Zb, and Zc is —CH$_2$CH$_2$— are slightly low in N-I transition point, but are more excellent in miscibility with other liquid crystalline compounds at low temperature compared with the compounds in which all Za, Zb, and Zc are single bond. Compounds in which at least one of bonding groups Za, Zb, and Zc is —COO— are slightly poor in voltage holding ratio, but have a high Δε compared with the compounds in which all Za, Zb, and Zc are single bond. Compounds in which at least one of bonding groups Za, Zb, and Zc is —CH$_2$CH$_2$CH$_2$CH$_2$— are slightly high in viscosity, but are more excellent in miscibility compared with the compounds in which all bonding groups Za, Zb, and Zc are single bond. Compounds in which at least one of bonding groups Za, Zb, and Zc is —CF$_2$O— are low in N-I transition point, but have a low viscosity and high Δε, and are chemically and electrically stable compared with the compounds in which all bonding groups Za, Zb, and Zc are single bond.

Preferable structure of terminal substituent Y and features of the compounds having the substituent are described as follows:

Compounds in which Y is F have a comparatively high Δε and low viscosity, and are excellent in miscibility with other liquid crystal compounds. Compounds in which Y is —CF$_3$ have a considerably high Δε. Compounds in which Y is —OCF$_3$ or —OCF$_2$H have a low viscosity. Compounds in which Y is Cl, —OCF$_2$CF$_2$H, or —OCF$_2$CFHCF$_3$ have a high Δn and high clearing point. Compounds in which Y is —OCH$_2$CF$_2$H, —OCH$_2$CF$_3$, or —OCFHCF$_3$ have a high N-I transition point and comparatively low viscosity.

Other preferable substituents as Y than those mentioned above include —CF$_2$H, —CF$_2$Cl, —CH$_2$CF$_3$, —CH$_2$CH$_2$F, —CH$_2$CH$_2$CH$_2$F, —CH$_2$CH$_2$CH$_2$CH$_2$F, —OCFH$_2$, —OCF$_2$Cl, —OCF$_2$CF$_3$, —OCF$_2$CF$_2$CF$_3$.

Substituents Q$_1$ to Q$_7$ to 1,4-phenylene group independently represent hydrogen atom, a halogen atom, or methyl group. The more halogen atoms or methyl groups the compounds have, the more excellent miscibility with other liquid crystalline compounds or liquid crystal compositions the compounds have; and the more hydrogen atoms the compounds have, the higher N-I transition point the compounds have. The more halogen atoms the compounds have at position Q$_2$, Q$_5$, and Q$_6$, the higher Δε the compounds have.

Any compounds of the present invention expressed by the general formula (1) have a comparatively high voltage holding ratio and have the features described above based on their partial structure. Among them, the compounds expressed by one of the formulas (1-A) to (1-R) have preferable characteristics.

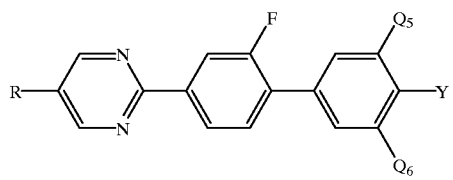

(1-A)

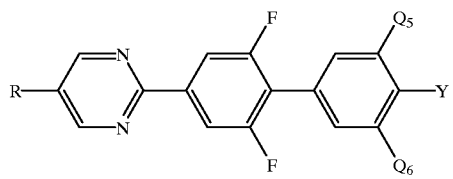

(1-B)

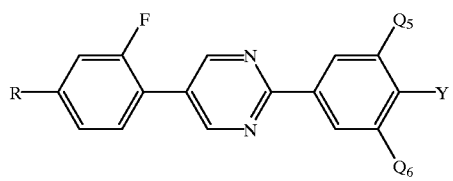

(1-C)

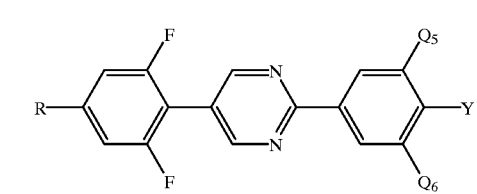
(1-D)
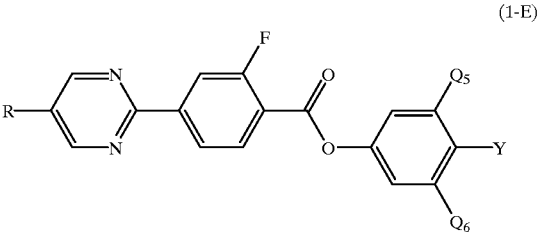
(1-E)
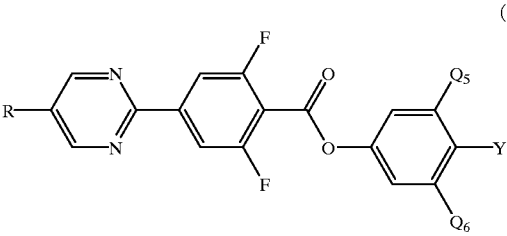
(1-F)
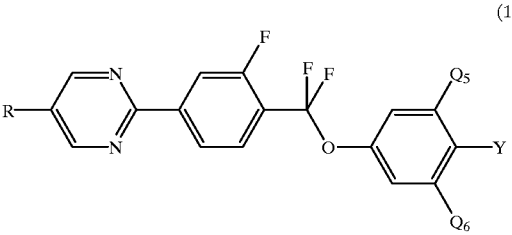
(1-G)
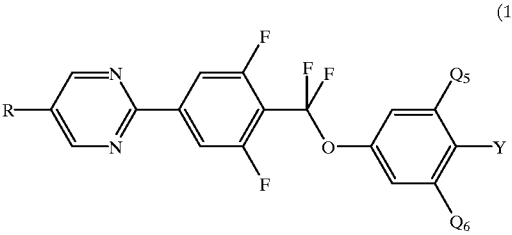
(1-H)
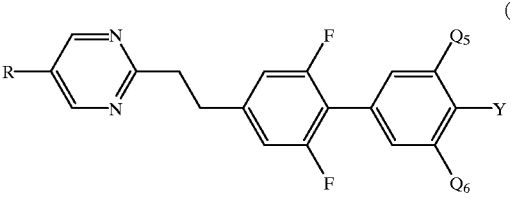
(1-I)
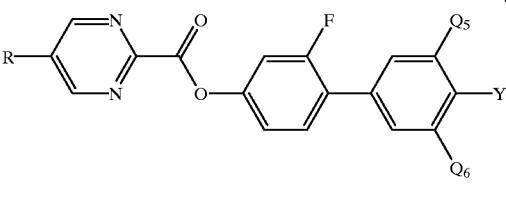
(1-J)
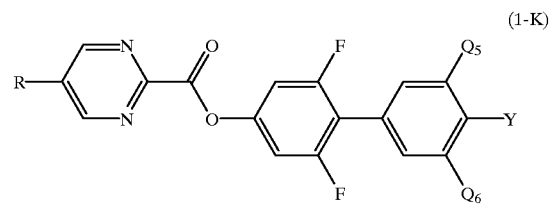
(1-K)
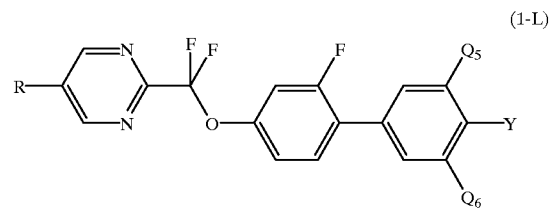
(1-L)
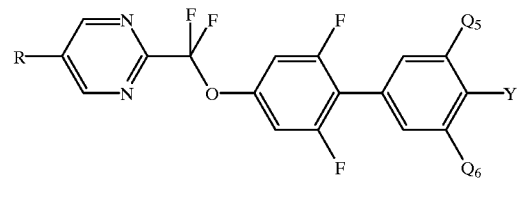
(1-M)
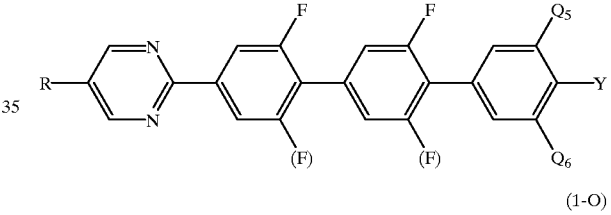
(1-N)
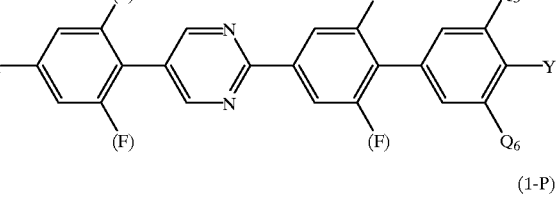
(1-O)
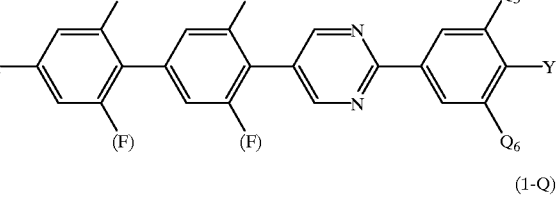
(1-P)
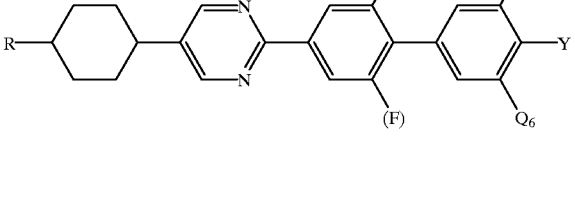
(1-Q)

-continued (1-R)

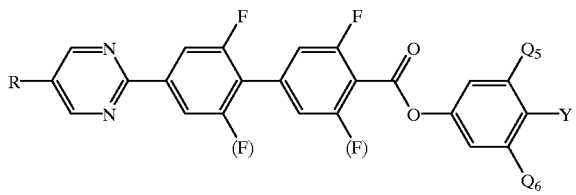

wherein R, $Q_5$, $Q_6$, and Y have the same meaning as described above.

Characteristics of the compounds expressed by one of the general formulas (1-A) to (1-R) are described below.

Compounds expressed by one of the general formulas (1-E), (1-F), (1-J), (1-K), and (1-R) have slightly poor voltage holding ratio, compared with other compounds, but any of them still have such a high degree of voltage holding ratio that the compounds can withstand the use for TFT type liquid crystal display devices. Further, since any of the compounds of the present invention have a high Δn, they are particularly useful as liquid crystal materials for liquid crystal display devices having a small cell thickness.

Compounds expressed by the general formula (1-A) or (1-B) are low in viscosity, have a high Δε, and are excellent in miscibility with other liquid crystalline compounds at low temperatures. When compounds of both formulas are compared, N-I transition point is higher with compounds of the general formula (1-A), Δε is higher with the compounds of the general formula (1-B), and viscosity is lower with (1-A).

Compounds expressed by the general formula (1-C) or (1-D) have a high Δε and are particularly excellent in miscibility with other liquid crystalline compounds at low temperatures. When compounds of both formulas are compared, N-I transition point is higher with (1-C), Δε is higher with (1-D), and viscosity is lower with (1-C).

Compounds expressed by one of the general formulas (1-E), (1F), (1-G), and (1-H) are characterized by having an extremely high Δε. When these compounds are compared, N-I transition point is higher with (1-E) and (1-F), and viscosity is lower with (1-G) and (1-H).

Compounds expressed by the general formula (1-I) are excellent in miscibility with other liquid crystalline compounds at low temperatures.

Compounds expressed by one of the general formulas (1-J), (1-K), (1-L), and (1-M) are characterized by having an extremely high Δε. When these compounds are compared, N-I transition point is higher with (1-J) and (1-K), and viscosity is lower with (1-L) and (1-M).

Since the compounds expressed by one of the general formulas (1-N) to (1-R) have an extremely high clearing point, they are useful as component of liquid crystal materials which can be used for displaying at high temperatures.

There has been no such compounds before that voltage holding ratio is high, Δε is high, and Δn is also high to the extent of the compounds of the present invention. Since the compounds of the present invention have such features as described above, they facilitate the production of liquid crystal display devices which have a small cell thickness and of which a high voltage holding ratio is required.

While the compounds of the present invention are preferable as liquid crystalline compounds for liquid crystal compositions for TFT, they can also desirably be used for many other applications such as liquid crystal composition for TN, G.H mode, polymer dispersion type liquid crystal display devices, dynamic scattering mode, STN, in-plane switching, OCB (Optically Compensated Birefringence) mode, or R-OCB mode; as ferroelectric liquid crystal compositions; and as anti-ferroelectric liquid crystal compositions.

Compounds expressed by the general formula (1) can be produced by using known procedures in organic synthesis in proper combination. For instance, they can be produced by the methods described in Jikken Kagaku Kouza (Course of Chemical Experiment) 4th edition (published by Maruzen Co., Ltd.) or Laid-open Japanese Patent Publication WO (Tokuhyo) No. Hei 4-501272.

Preferable procedures for synthesizing typical compounds are shown below. Synthesis method of the compounds expressed by the general formula (1-A), (1-B), or (1-O):

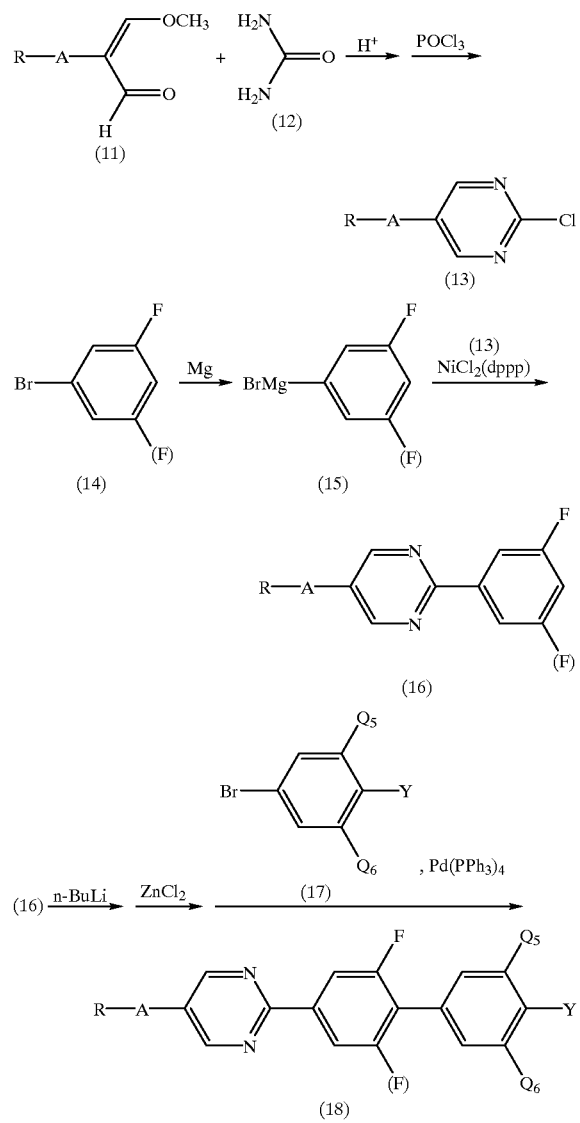

A compound expressed by the general formula (11) is reacted with urea under an acidic condition, and then the product thus obtained is reacted with a chlorinating agent such as phosphorus oxychloride to obtain a compound expressed by the general formula (13). Grignard reagent of the formula (15) prepared from a compound of the formula (14) and magnesium is reacted with the compound expressed by the general formula (13) in the presence of NiCl$_2$ (dppp) to obtain a compound of the general formula (16). The compound of the general formula (16) is lithiated with a lithiating agent such as butyl lithium, and the lithiated product is reacted with zinc chloride, Pd(O), and a compound of the general formula (17) to obtain a compound expressed by the general formula (18).

This method employs a method described in J. Org. Chem., 42, 1821 (1977). Also, a method described in J. Chem. Soc. Perkin Trans. 2, 2041 (1989) can be used.

General formula (18) includes the general formulas (1-A), (1-B), and (1-O).

Synthesis method of the compounds expressed by the general formula (1-C), (1-D), or (1-P):

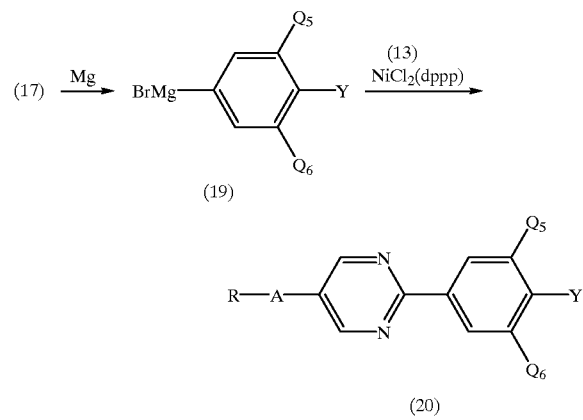

Compounds expressed by the general formula (20) are obtained in the same manner as in the step in which the compound of the general formula (16) described above is obtained with the exception that a compound of the general formula (17) is used in place of the compound of the formula (14).

General formula (20) includes the general formulas (1-C), (1-D), and (1-P).

Synthesis method expressed by the general formula (1-E) or (1-F):

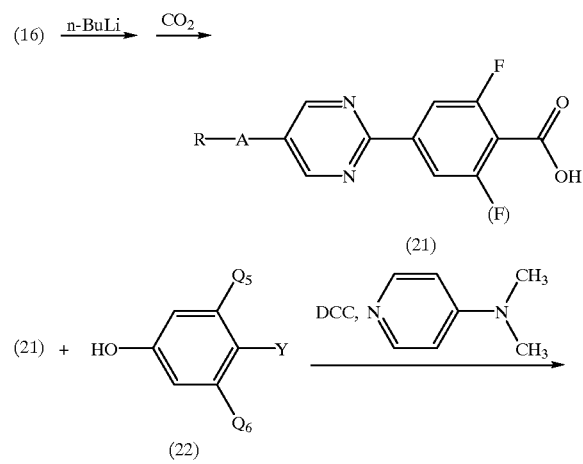

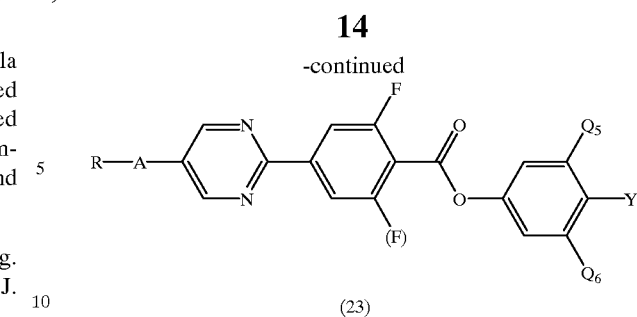

Compound of the general formula (16) is lithiated with a lithiating agent such as butyl lithium, and then the lithiated product is reacted with carbon dioxide to obtain a compound of the general formula (21). The compound of the general formula (21) and a phenol derivative expressed by the general formula (22) are reacted in the presence of dicyclohexylcarbodiimide and 4-(dimethylamino)pyridine to obtain a compound expressed by the general formula (23).

The general formula (23) includes the general formulas (1-E) and (1-F). This method is described in Jikken Kagaku Kouza (Course of Chemical Experiment) 4th edition, vol. 22, p 46.

Synthesis method of the compounds expressed by the general formula (1-G) or (1-H):

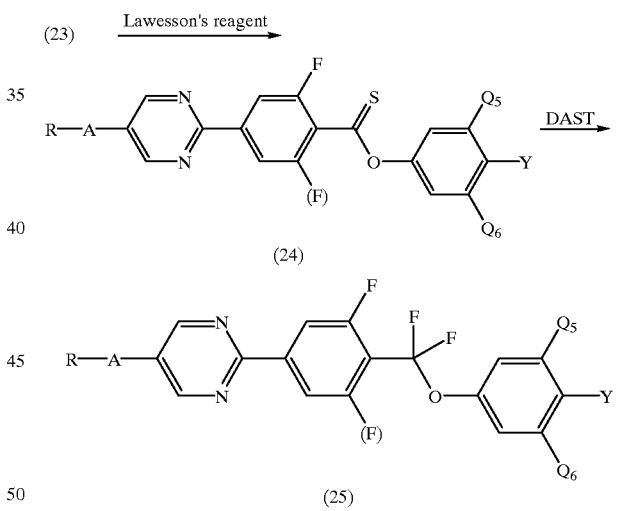

Compound of the general formula (23) is reacted with Lawesson's reagent to obtain a compound expressed by the general formula (24). Then, the compound of the general formula (24) is reacted with a fluorinating reagent such as diethylaminosulfur trifluoride (DAST) and a solution of hydrofluoric acid in pyridine to obtain a compound expressed by the general formula (25).

General formula (25) includes the general formulas (1-G) and (1-H).

Synthesis method of the compounds expressed by the general formula (1-I):

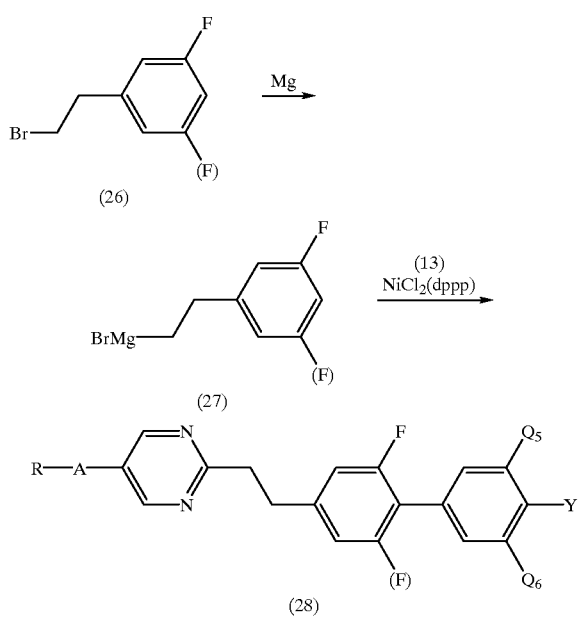

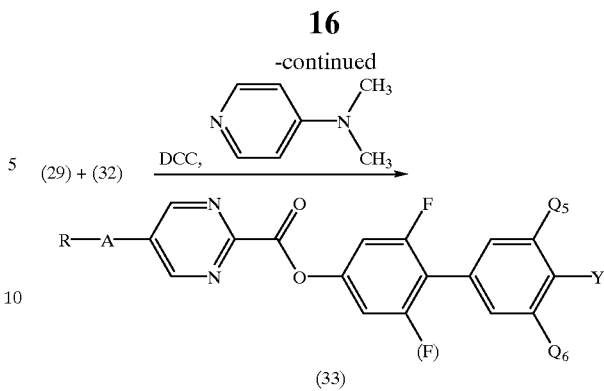

Compounds expressed by the general formula (28) are obtained in the same manner as in the step in which the compound of the general formula (18) described above is obtained with the exception that a compound of the formula (26) is used in place of the compound of the formula (14).

General formula (28) includes the general formula (1-I).

Synthesis method of the compounds expressed by the general formula (1-J) or (1-K):

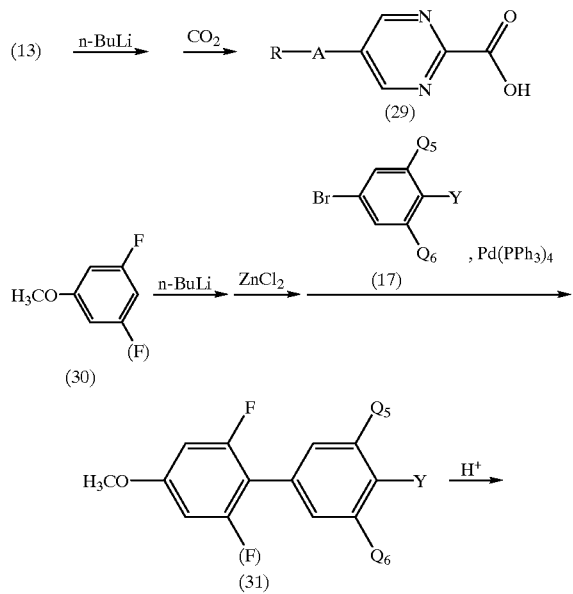

Compounds expressed by the general formula (29) are obtained in the same manner as in the step in which the compound of the general formula (21) is obtained with the exception that a compound of the general formula (13) is used in place of the compound of the general formula (16).

Compounds expressed by the general formula (31) are obtained in the same manner as in the step in which the compound of the general formula (18) is obtained with the exception that a phenol derivative of the formula (30) in which hydroxy group is protected is used in place of the compound of the general formula (16). Compounds expressed by the general formula (32) are obtained by treating a compound of the general formula (31) with an acid.

Compounds expressed by the general formula (33) are obtained in the same manner as in the step in which the compound of the general formula (23) described above is obtained with the exception that a compound of the general formula (29) is used in place of the compound of the general formula (21) and that a compound of the general formula (32) is used in place of the compound of the general formula (22). General formula (33) includes the general formulas (1-J) and (1-K).

Synthesis method of the compounds expressed by the general formula (1-K) or (1-M):

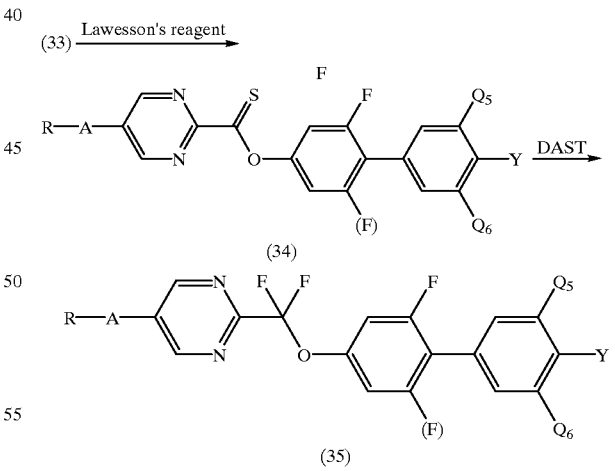

Compounds expressed by the general formula (35) are obtained in the same manner as in the step in which the compound of the general formula (25) is obtained with the exception that a compound of the general formula (33) is used in place of the compound of the general formula (23).

General formula (35) includes the general formulas (1-L) and (1-M).

Synthesis method of the compounds expressed by the general formula (1-N):

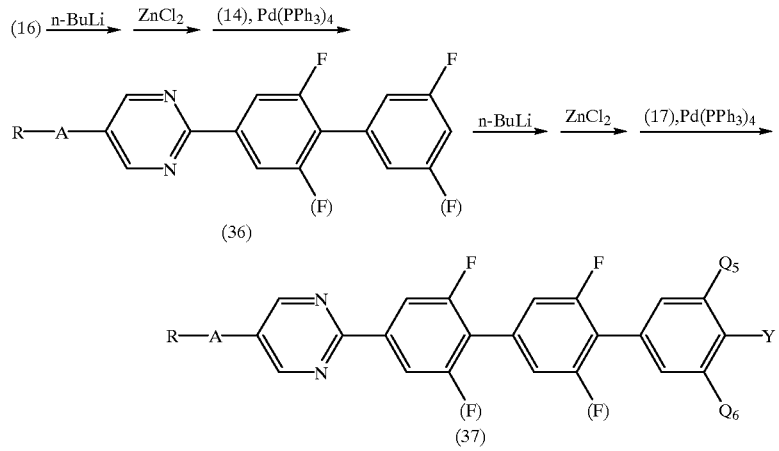

Compounds expressed by the general formula (36) are obtained in the same manner as in the step in which the compound of the general formula (18) described above is obtained with the exception that a compound of the formula (14) is used in place of the compound of the general formula (17).

Compounds of the general formula (37) are obtained in the same manner as in the step in which the compound of the general formula (18) is obtained with the exception that a compound of the general formula (36) is used in place of the compound of the general formula (16).

General formula (37) includes the general formula (1-N).

Synthesis method of the compounds expressed by the general formula (1-R):

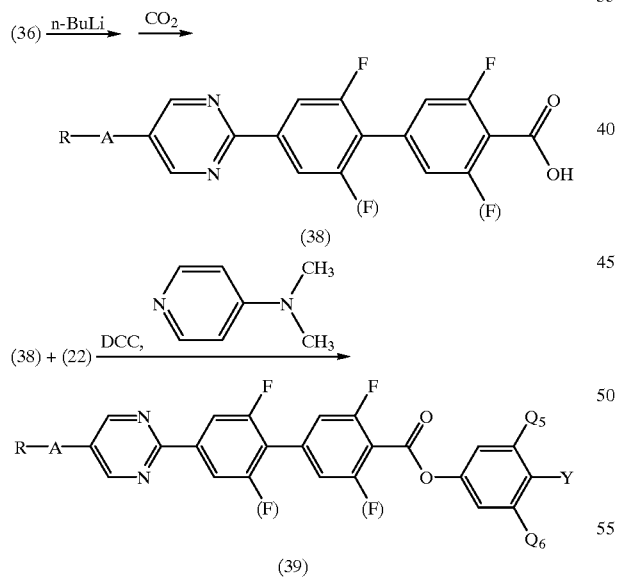

Compounds expressed by the general formula (39) are obtained in the same manner as in the step in which the compound of the general formula (23) is obtained with the exception that a compound of the general formula (36) is used in place of the compound of the general formula (16).

General formula (39) includes the general formula (1-R).

Liquid crystal compositions of the present invention preferably comprises at least one compound (pyrimidine derivative) expressed by the general formula (1) in the ratio of 0.1 to 99.9% by weight to develop excellent characteristics, and the ratio is more preferably 1 to 50% by weight and still more desirably 3 to 20% by weight.

Liquid crystal compositions of the present invention comprises compounds selected from the group consisting of the compounds expressed by one of the general formulas (2) to (9) depending on the purposes of the liquid crystal compositions, in addition to a first component comprising at least one compound expressed by the general formula (1) to achieve the objects of the invention.

As preferable examples of the compounds used in the liquid crystal compositions of the present invention and expressed by one of the general formulas (2) to (4), the following compounds can be mentioned:

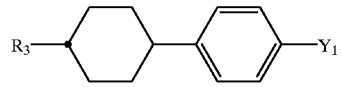
(2-1)

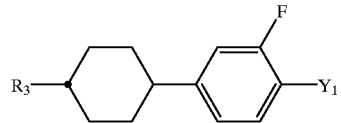
(2-2)

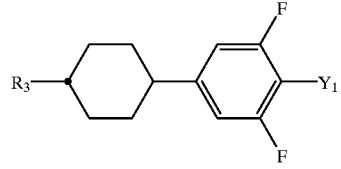
(2-3)

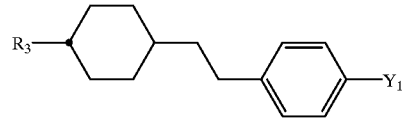
(2-4)

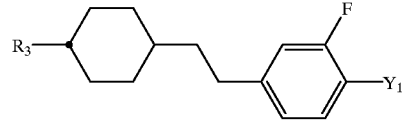
(2-5)

(2-6) 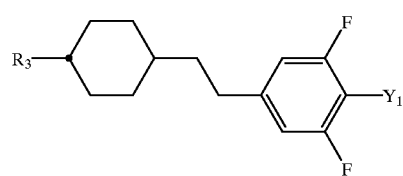
(2-7) 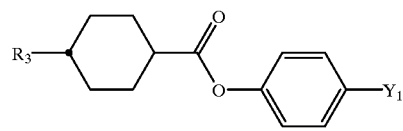
(2-8) 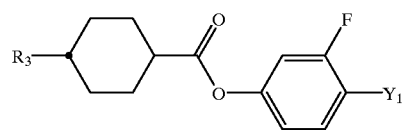
(2-9) 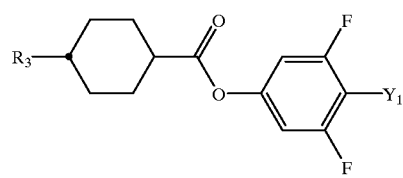
(3-1) 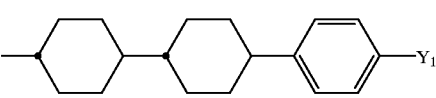
(3-2) 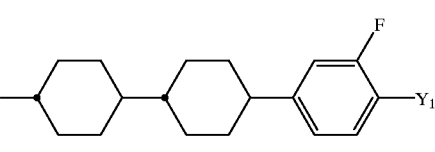
(3-3) 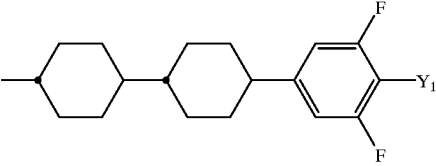
(3-4) 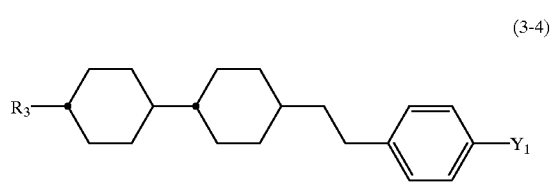
(3-5) 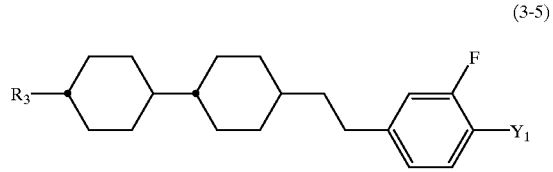
(3-6) 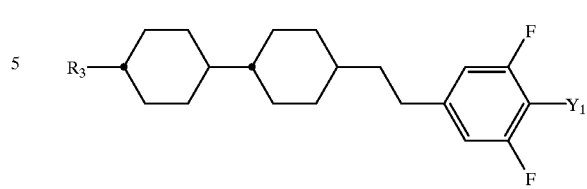
(3-7) 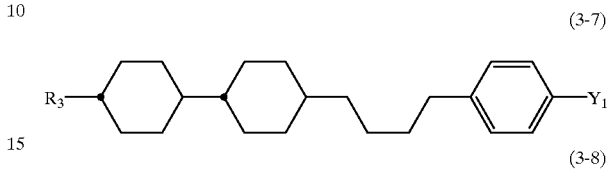
(3-8) 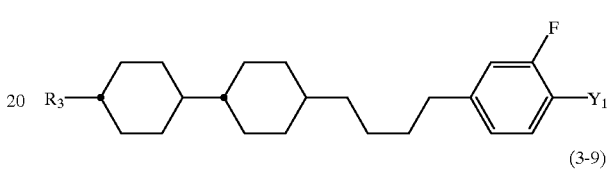
(3-9) 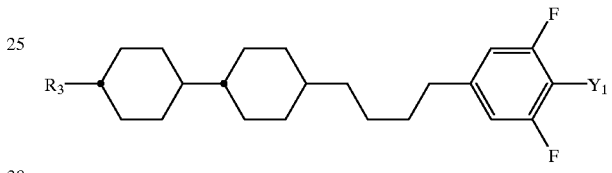
(3-10) 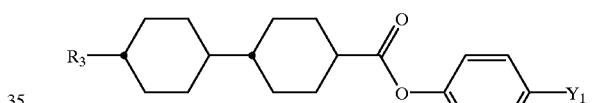
(3-11) 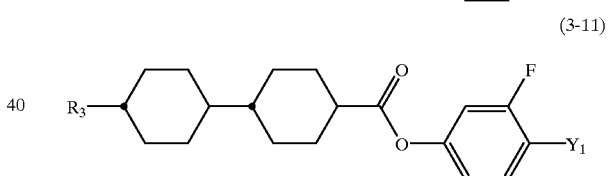
(3-12) 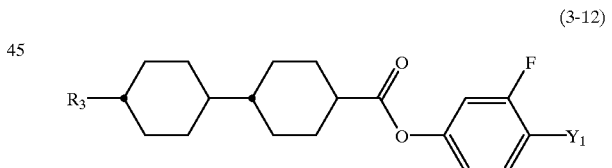
(3-13) 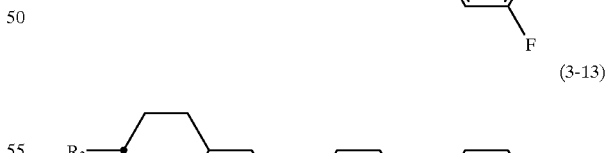
(3-14) 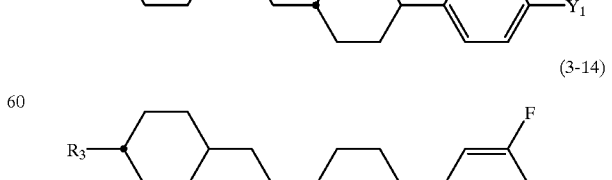

(3-15)
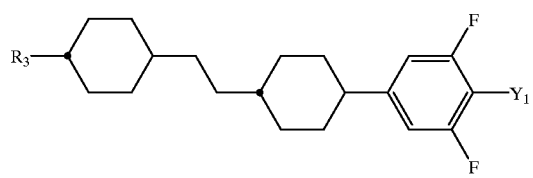
(3-16)
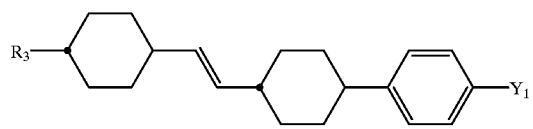
(3-17)
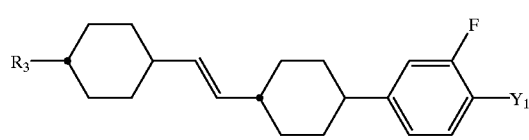
(3-18)
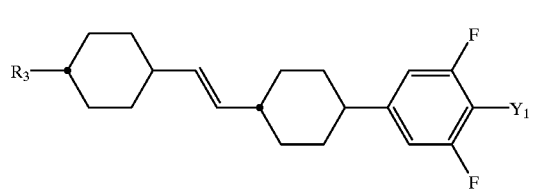
(3-19)
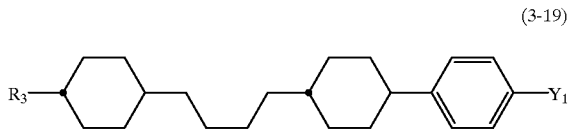
(3-20)
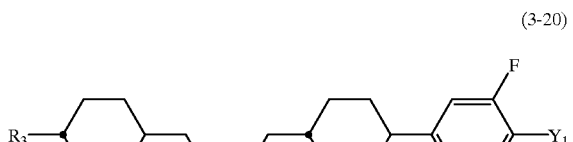
(3-21)
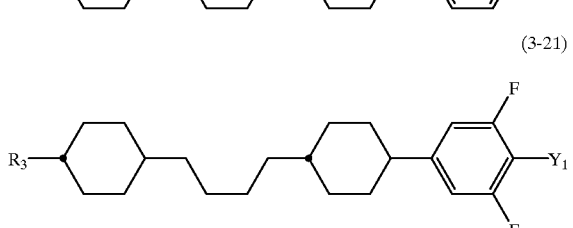
(3-22)
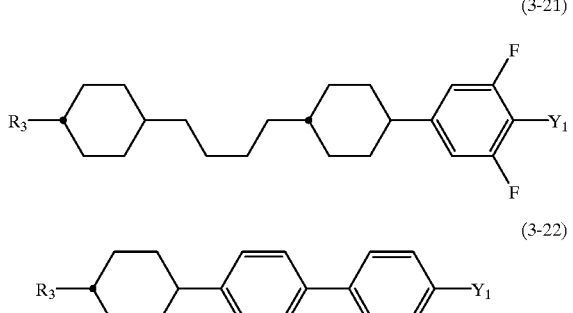
(3-23)
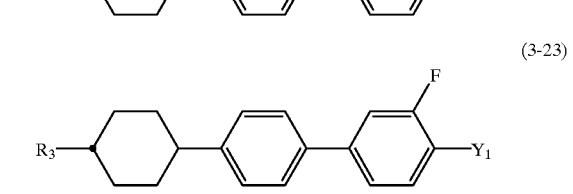
(3-24)
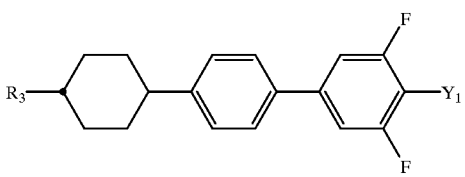
(3-25)
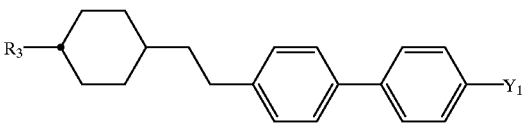
(3-26)
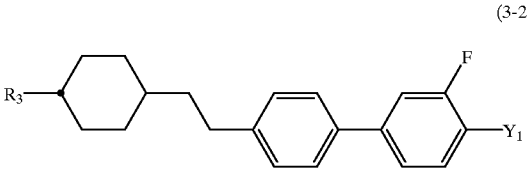
(3-27)
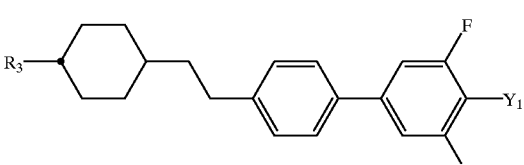
(3-28)
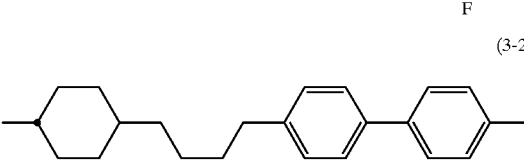
(3-29)
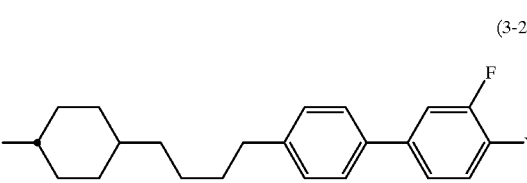
(3-30)
(3-31)
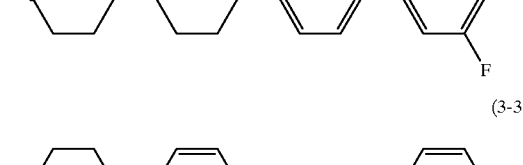
(3-32)
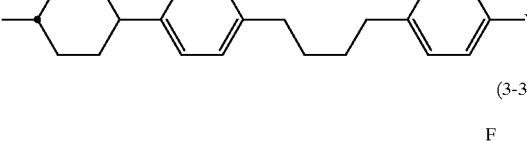
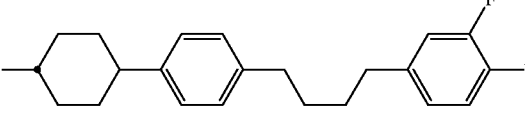

(3-33)
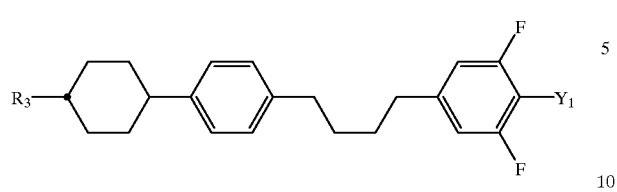
(3-34)
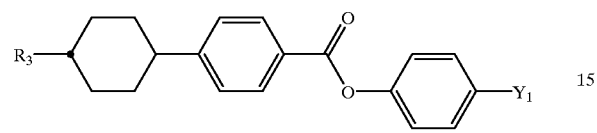
(3-35)
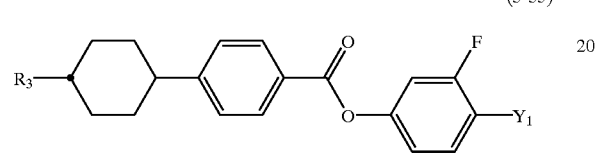
(3-36)
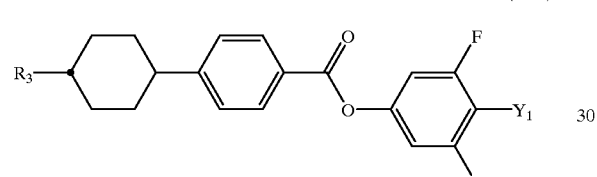
(3-37)
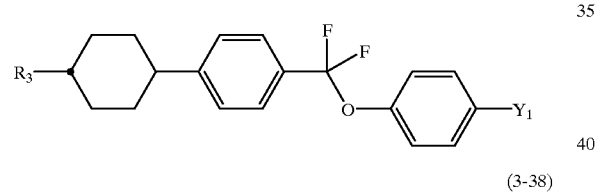
(3-38)
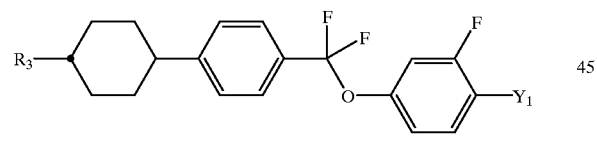
(3-39)
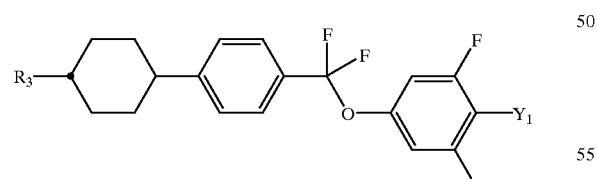
(3-40)
(3-41)
(3-42)
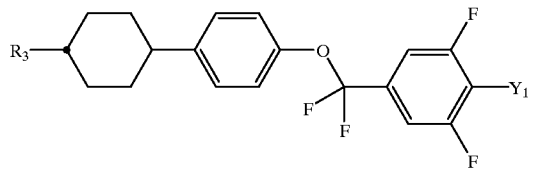
(3-43)
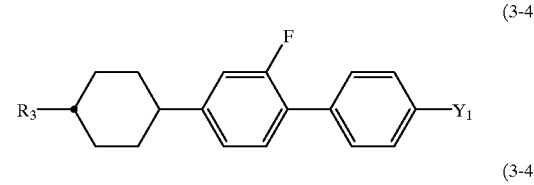
(3-44)
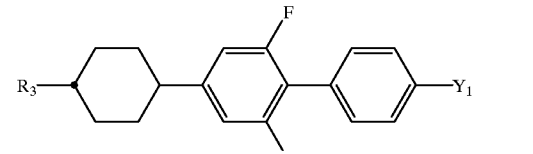
(3-45)
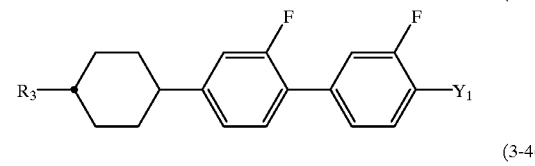
(3-46)
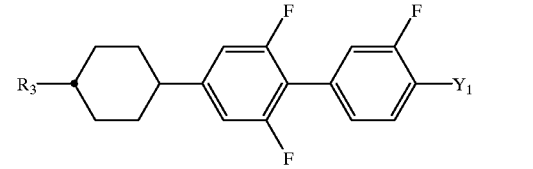
(3-47)
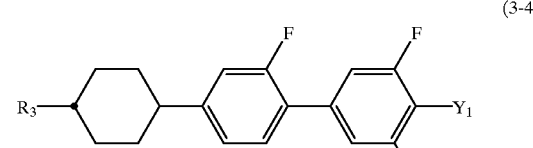
(3-48)
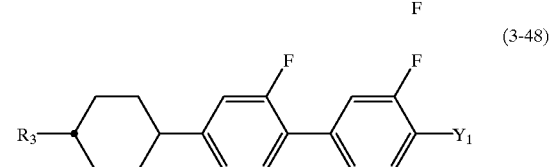
(3-49)
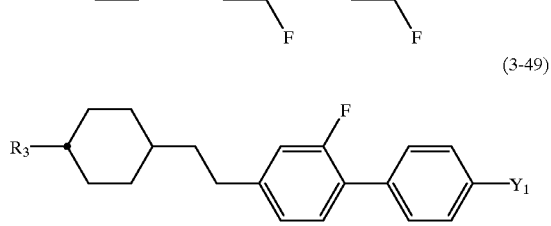

(3-50) 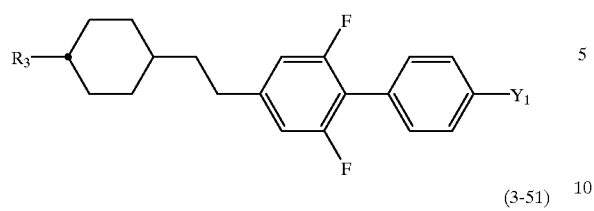
(3-51) 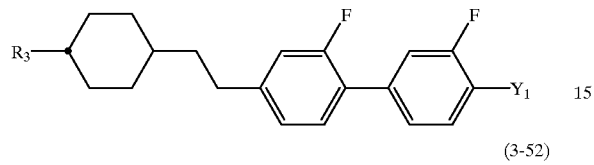
(3-52) 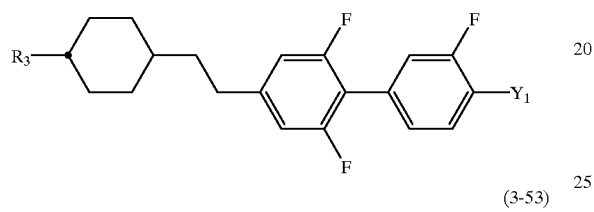
(3-53) 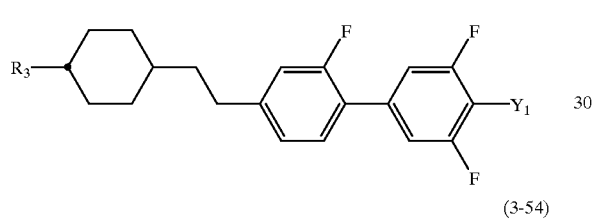
(3-54) 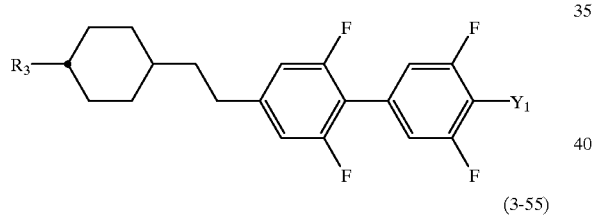
(3-55) 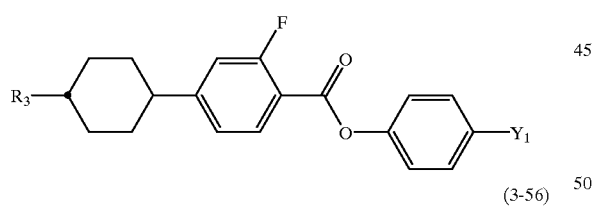
(3-56) 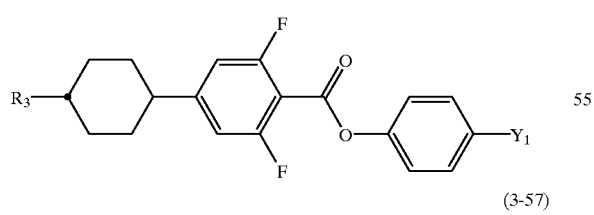
(3-57) 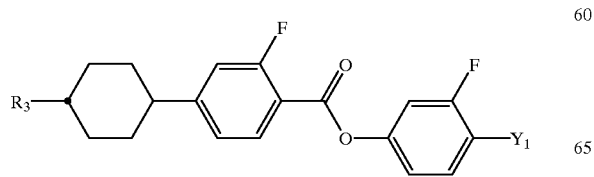
(3-58) 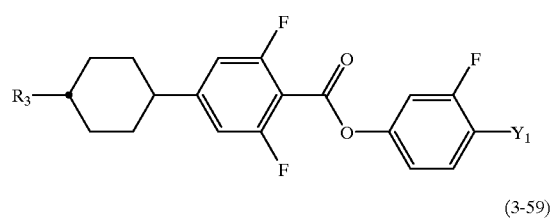
(3-59) 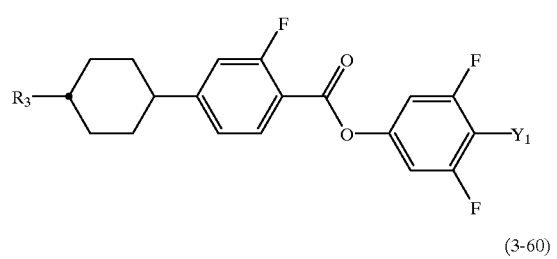
(3-60) 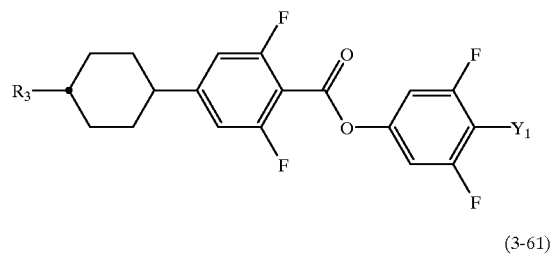
(3-61) 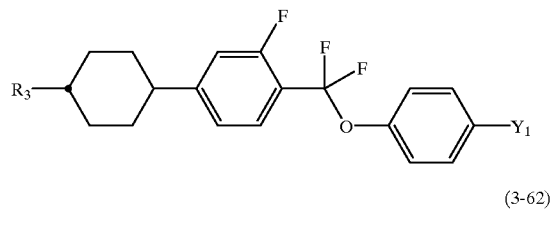
(3-62) 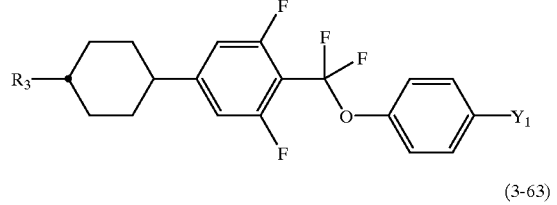
(3-63) 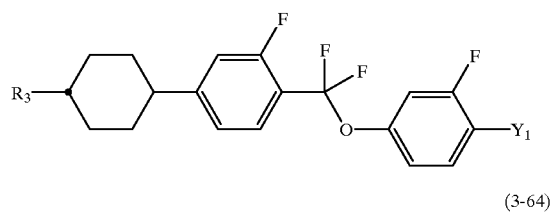
(3-64) 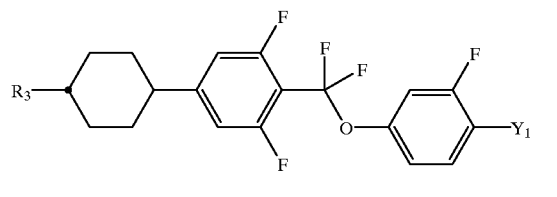

(3-65)
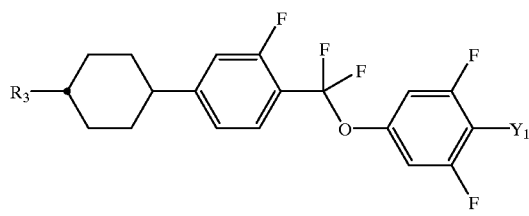
(3-66)
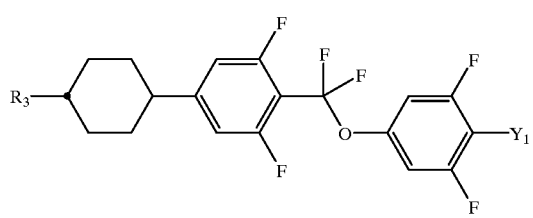
(3-67)
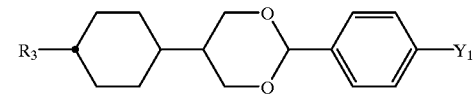
(3-68)
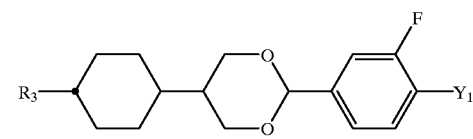
(3-69)
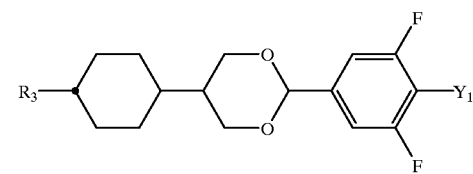
(4-1)
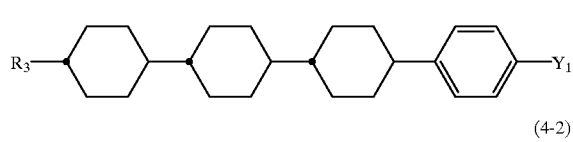
(4-2)
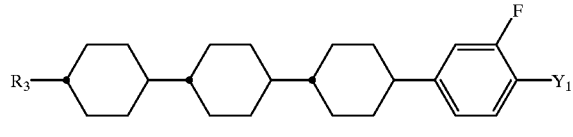
(4-3)
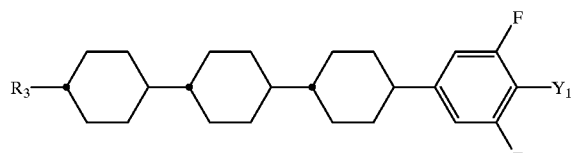
(4-4)
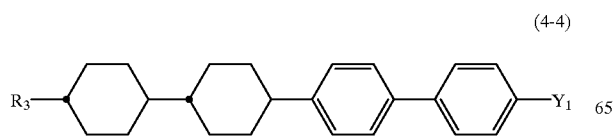
(4-5)
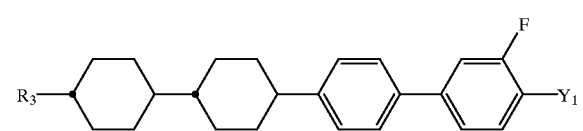
(4-6)
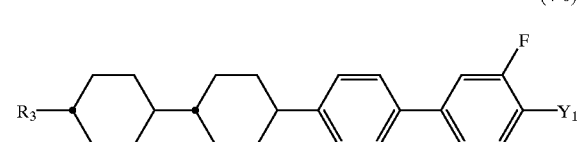
(4-7)
(4-8)
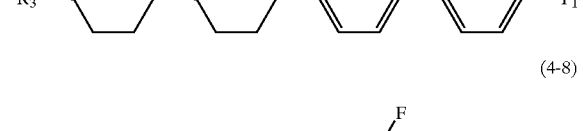
(4-9)
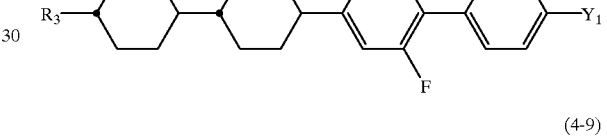
(4-10)
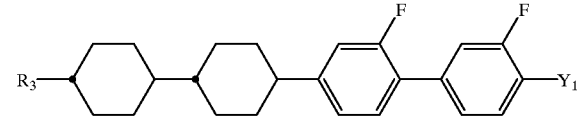
(4-11)
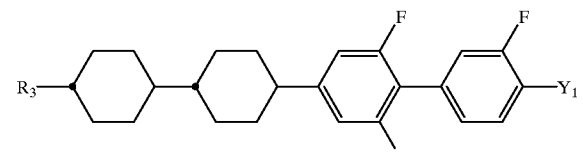
(4-12)
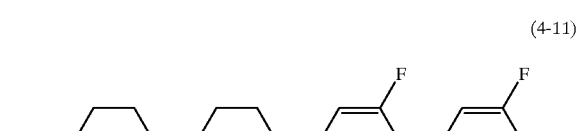

(4-13) 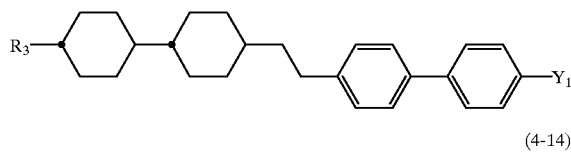

(4-14) 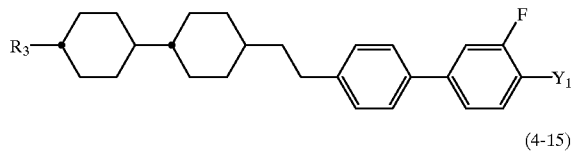

(4-15) 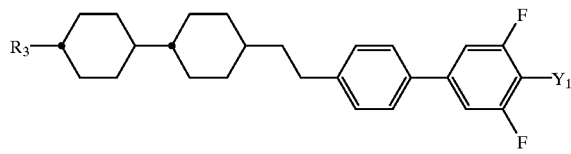

(4-16) 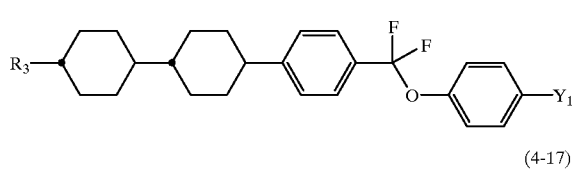

(4-17) 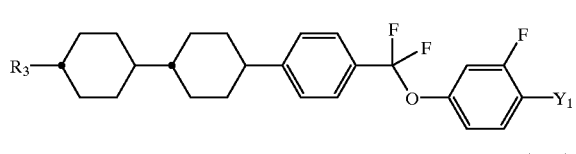

(4-18) 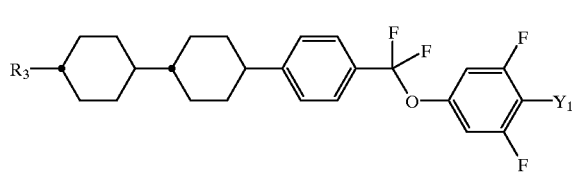

(4-19) 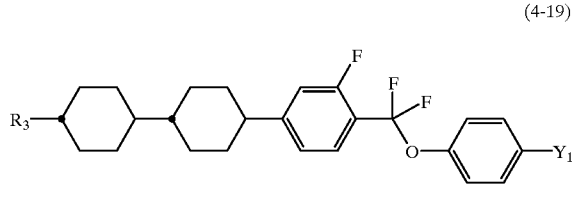

(4-20) 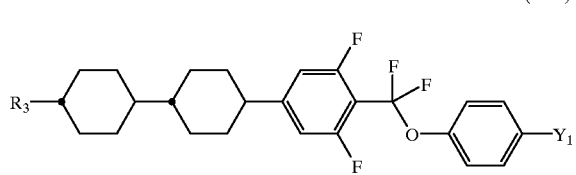

(4-21) 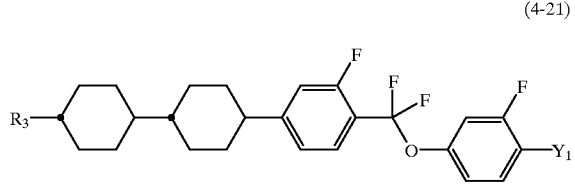

(4-22) 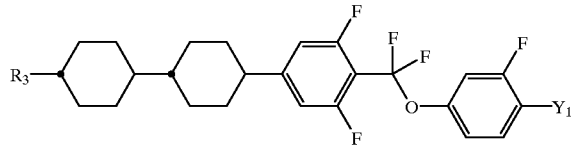

(4-23) 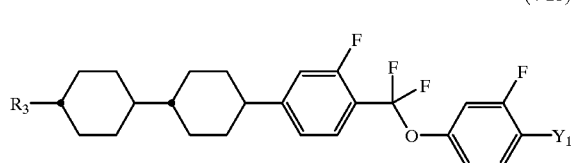

(4-24) 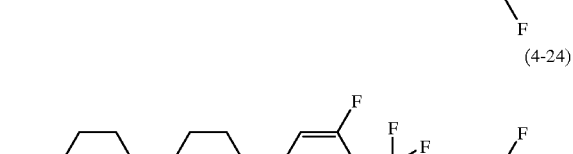

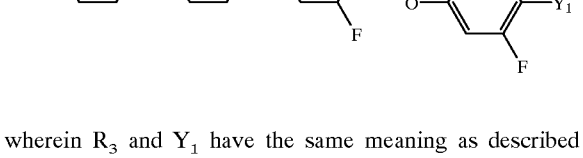

wherein $R_3$ and $Y_1$ have the same meaning as described above.

Compounds expressed by one of the general formulas (2) to (4) have a positive dielectric anisotropy value, are excellent in thermal stability and chemical stability, and are extremely useful when liquid crystal compositions for TFT are produced of which such a high reliability that liquid crystal compositions have a high voltage holding ratio (or large specific resistance) is required.

When liquid crystal compositions for TFT are produced, the compounds expressed by one of the general formulas (2) to (4) can be used in the range of 1 to 99% by weight based on the total amount of liquid crystal composition, and the range is preferably 10 to 97% by weight and more desirably 40 to 95% by weight. At that time, compounds expressed by one of the general formulas (7) to (9) can further be included in liquid crystal compositions for the purpose of adjusting viscosity.

Even when liquid crystal compositions for STN or TN, compounds expressed by one of the general formulas (2) to (4) can be used.

As preferable examples of the compounds used in the liquid crystal compositions of the present invention and expressed by the general formula (5) or (6), the following compounds can be mentioned:

(5-1) 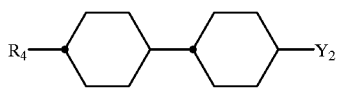

(5-2) 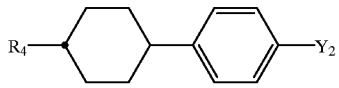

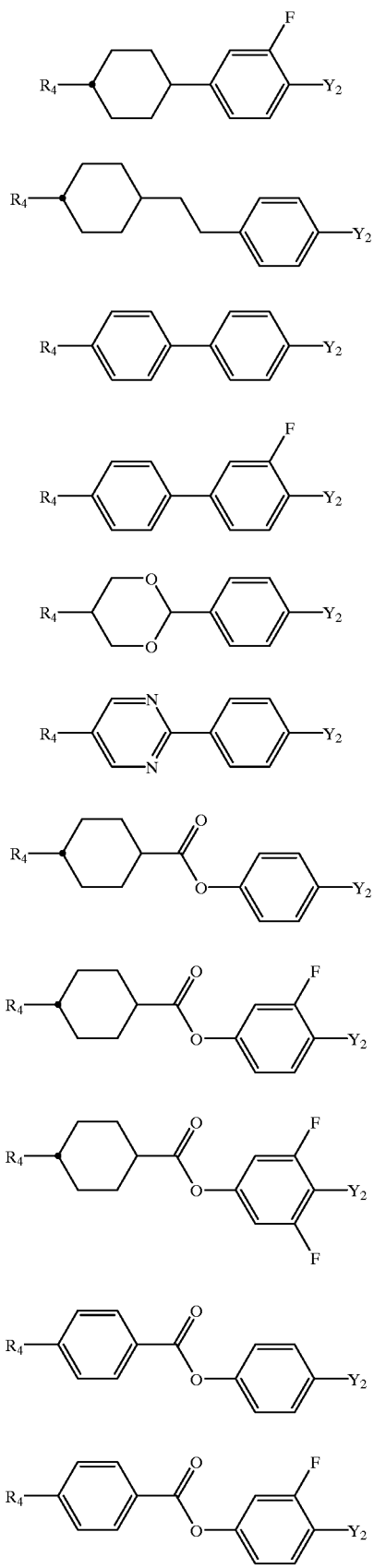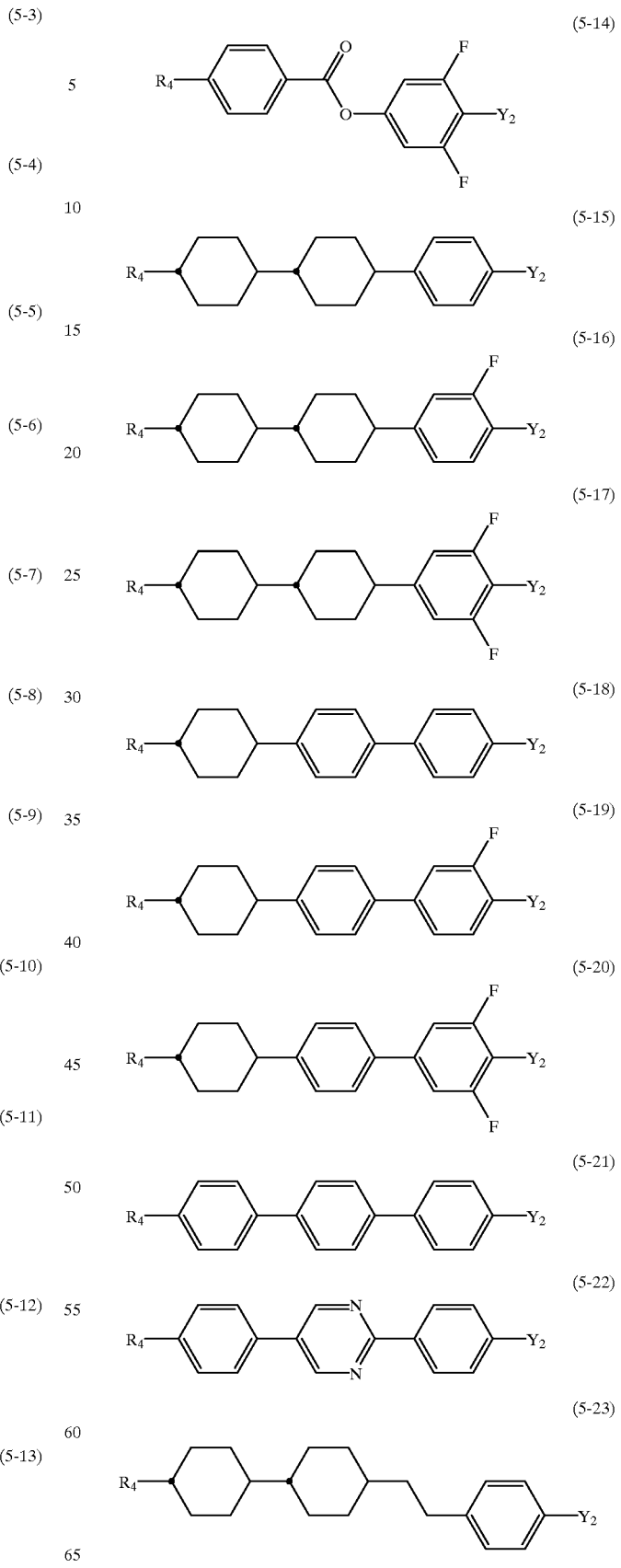

(5-24) 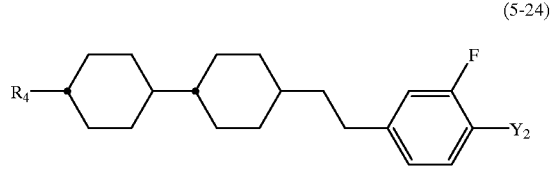
(5-25) 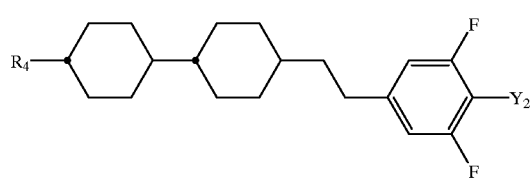
(5-26) 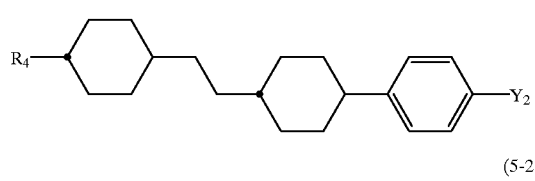
(5-27) 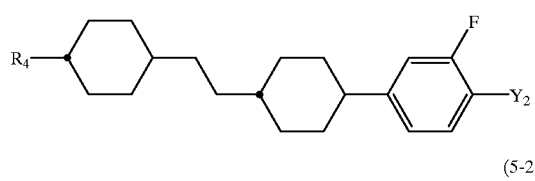
(5-28) 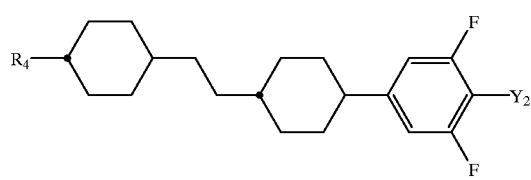
(5-29) 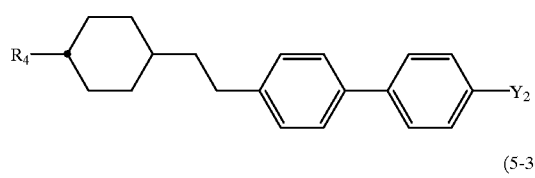
(5-30) 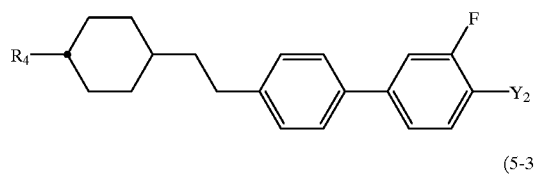
(5-31) 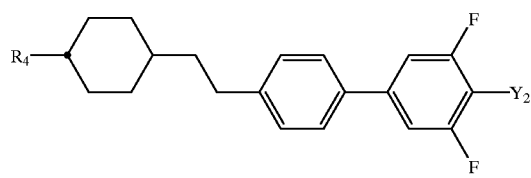
(5-32) 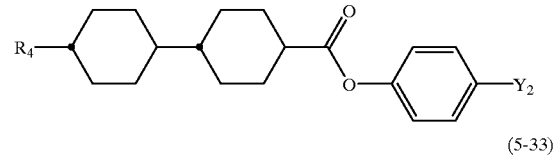
(5-33) 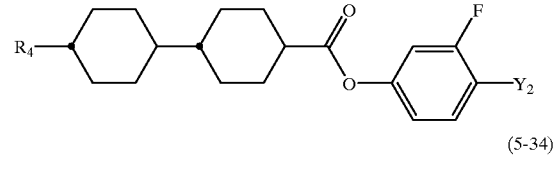
(5-34) 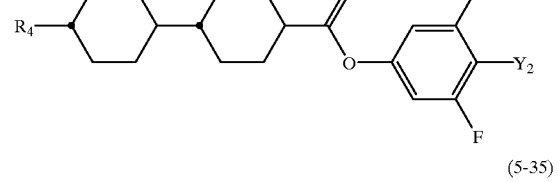
(5-35) 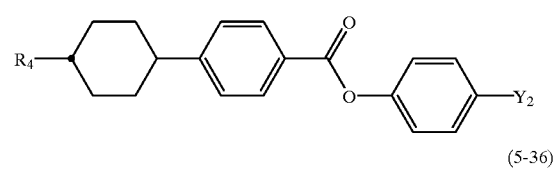
(5-36) 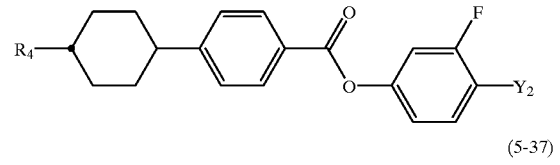
(5-37) 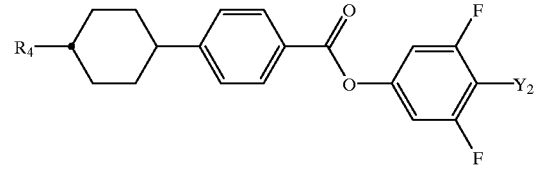
(5-38) 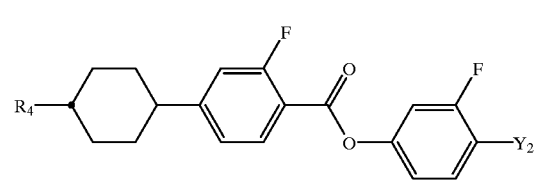
(5-39) 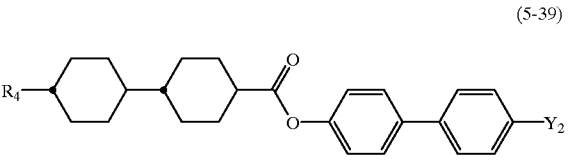
(5-40)

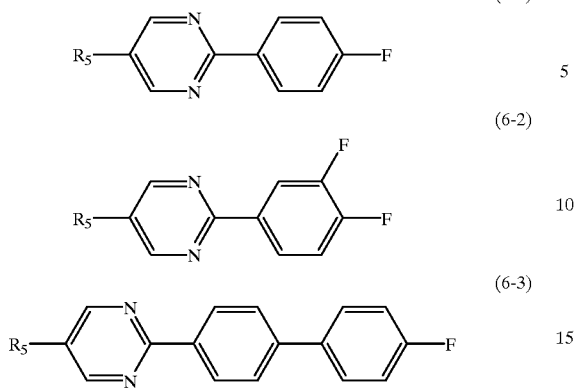

(6-1)

(6-2)

(6-3)

wherein $R_4$, $R_5$, and $Y_2$ have the same meaning as described above.

Compounds expressed by the general formula (5) or (6) have a large positive dielectric anisotropy value and are used particularly for the purpose of lowering threshold voltage of liquid crystal compositions. Also, they are used for the purpose of adjusting optical anisotropy value and widening nematic range such as raising clearing point. Further, they are used for the purpose of improving steepness of voltage-transmittance curve of liquid crystal compositions for STN or TN.

Compounds expressed by the general formula (5) or (6) are particularly useful when liquid crystal compositions for STN or TN are produced.

When the amount of the compounds expressed by the general formula (5) or (6) is increased in liquid crystal compositions, threshold voltage of liquid crystal compositions lowers but viscosity increases. Accordingly, so fa as the viscosity of liquid crystal compositions satisfies a required value, it is advantageous to use the compounds in a large amount, since display devices can be driven at a low voltage. When liquid crystal compositions for STN or TN are produced, compounds expressed by the general formula (5) or (6) can be used in the range of 0.1 to 99.9% by weight based on the total amount of liquid crystal composition, and the range is preferably 10 to 97% by weight and more desirably 40 to 95% by weight.

As preferable examples of the compounds used in the liquid crystal compositions of the present invention and expressed by one of the general formulas (7) to (9), the following compounds can be mentioned:

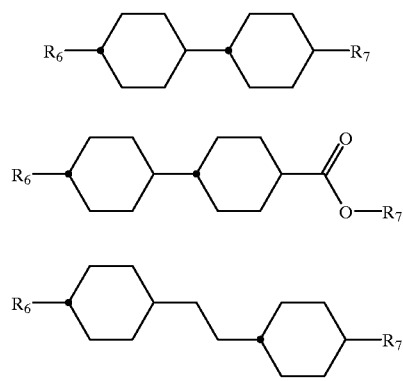

(7-1)

(7-2)

(7-3)

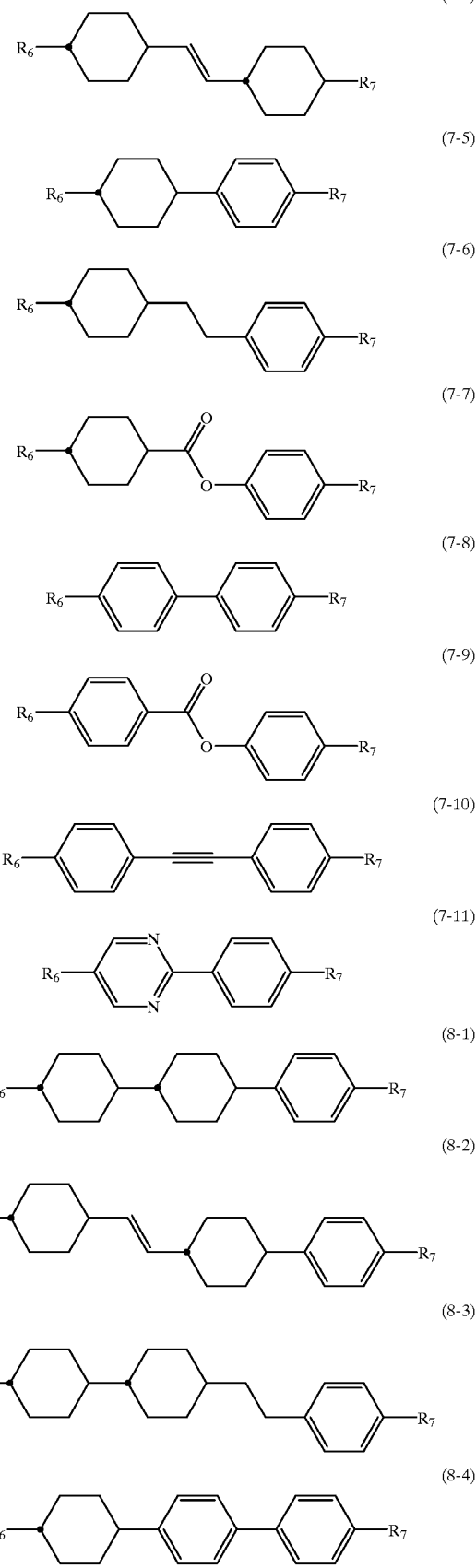

(7-4)

(7-5)

(7-6)

(7-7)

(7-8)

(7-9)

(7-10)

(7-11)

(8-1)

(8-2)

(8-3)

(8-4)

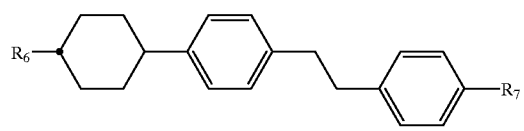
(8-5)
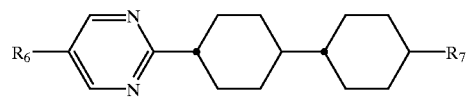
(8-6)
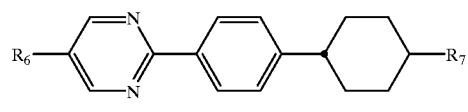
(8-7)
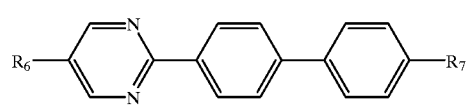
(8-8)
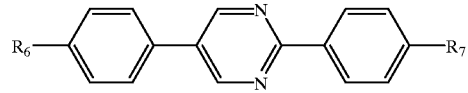
(8-9)
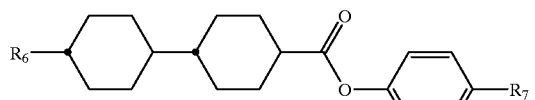
(8-10)
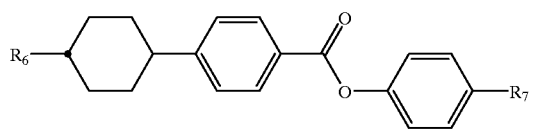
(8-11)
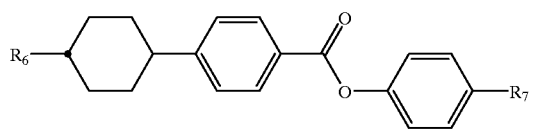
(8-12)
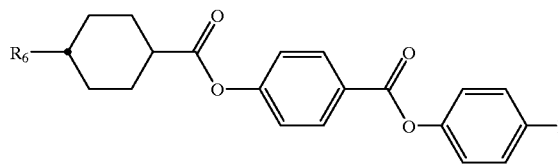
(8-13)
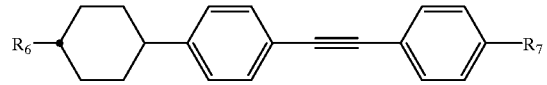
(8-14)
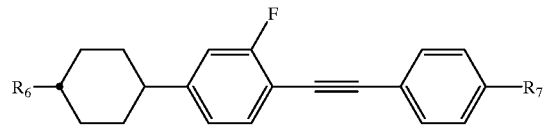
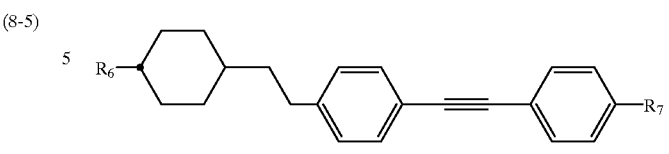
(8-15)
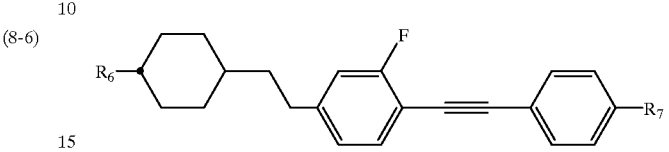
(8-16)
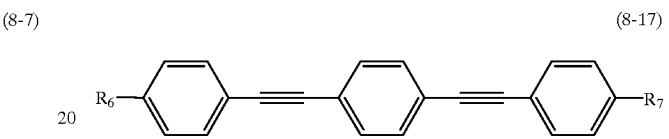
(8-17)
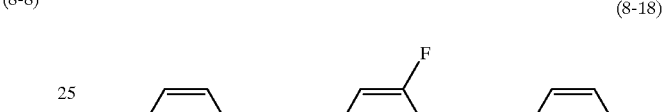
(8-18)
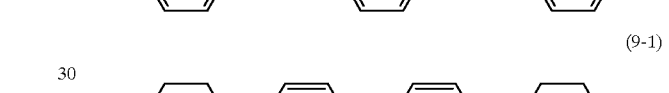
(9-1)
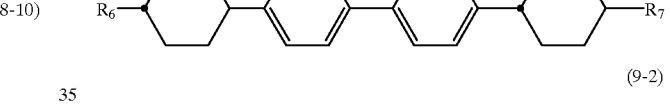
(9-2)
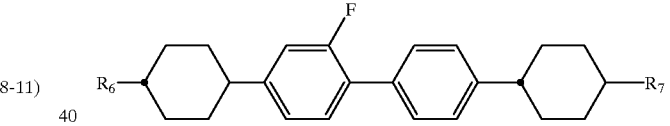
(9-3)
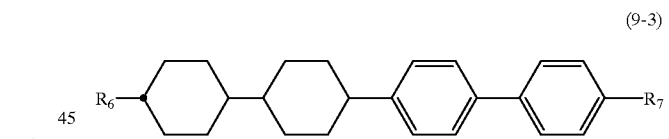
(9-4)
(9-5)
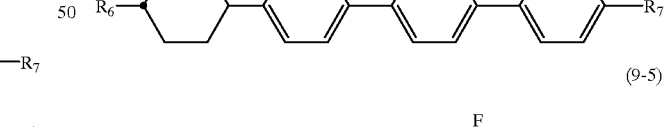
(9-6)
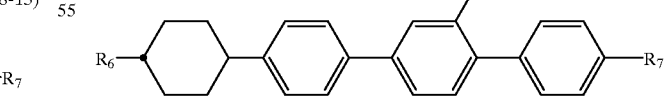
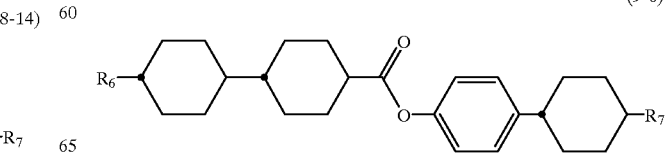
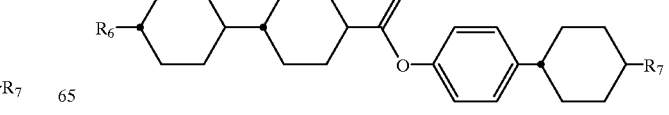

wherein $R_6$ and $R_7$ have the same meaning as described above.

Compounds expressed by one of the general formulas (7) to (9) have a small absolute value of dielectric anisotropy, and the value is close to 0. Compounds of the general formula (7) are used principally for the purpose of adjusting viscosity and adjusting optical anisotropy value. Compounds expressed by the general formula (8) or (9) are used for the purpose of widening nematic range such as raising clearing point or for the purpose of adjusting optical anisotropy value.

When the amount of the compounds expressed by one of the general formulas (7) to (9) is increased in liquid crystal compositions, threshold voltage of liquid crystal compositions rises but viscosity reduces. Accordingly, so far as threshold voltage of liquid crystal compositions satisfies a required value, it is desirable to use the compounds in a large amount. When liquid crystal compositions for TFT are produced, the amount of the compounds expressed by one of the general formulas (7) to (9) to be used is preferably less than 40% by weight and more desirably less than 35% by weight. When liquid crystal compositions for STN or TN are produced, the amount of the compounds to be used is preferably less than 70% by weight and more desirably less than 60% by weight.

Except such specific cases as liquid crystal compositions for OCB (Optically Compensated Birefringence) mode, an optically active compound is usually added to liquid crystal compositions in the present invention for the purpose of inducing helical structure of liquid crystals to adjust required twisting angle and to prevent reverse twist. While any known optically active compounds can be used for such purposes, the following optically active compounds (Op-1) to (Op-8) can be mentioned as preferable examples:

(Op-1)
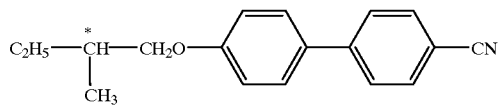

(Op-2)
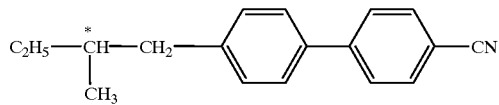

(Op-3)
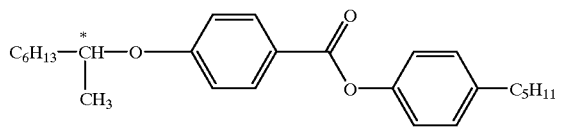

(Op-4)
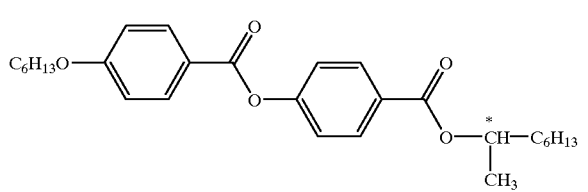

-continued (Op-5)
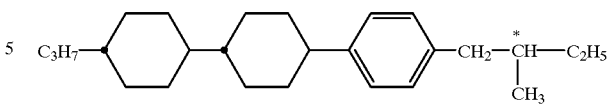

(Op-6)
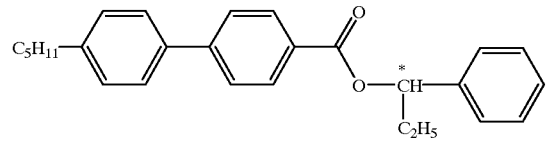

(Op-7)
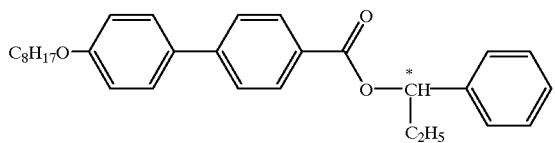

(Op-8)
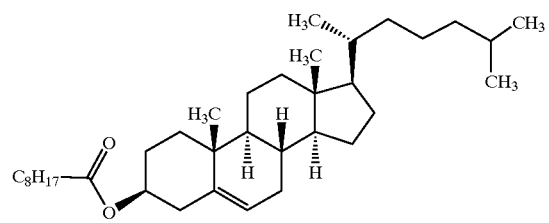

Usually, one of these optically active compounds is added to the liquid crystal compositions of the present invention to adjust the pitch of the helical twist of liquid crystals. The pitch is preferably adjusted in the range of 40 to 200 $\mu$m in the case of liquid crystal compositions for TFT or TN. In the case of liquid crystal compositions for STN, the pitch is preferably adjusted in the range of 6 to 20 $\mu$m. In the case of liquid crystal compositions for bistable TN mode, the pitch is preferably adjusted in the range of 1.5 to 4 $\mu$m. Further, two or more kind of optically active compounds may be added for the purpose of adjusting the dependency of the pitch on temperature.

Liquid crystal compositions of the present invention can be used as ones for guest-host (GH) mode by adding a dichroic dye such as merocyanine type, styryl type, azo type, azomethine type, azoxy type, quinophthalone type, anthraquinone type, or tetrazine type dye. Alternatively, liquid crystal compositions of the present invention can be used as ones for NCAP which is prepared by the microencapsulation of a nematic liquid crystal, or for a polymer dispersed liquid crystal display device (PDLCD) represented by polymer network liquid crystal display device (PNLCD) prepared by forming polymers of three-dimensional reticulated structure in a liquid crystal. In addition, the liquid crystal compositions of the present invention can be used as ones for electrically controlled birefringence (ECB) mode or for dynamic scattering (DS) mode.

Liquid crystal compositions of the present invention can be produced by conventional methods. Generally, a method wherein various components are dissolved in each other at a high temperature is adopted.

As examples of liquid crystal compositions comprising the liquid crystalline compound of the present invention, the following composition examples (Composition Examples 1 through 18) can be mentioned. In the composition examples, compounds are designated by symbolizing each part of molecules, that is, left side terminal group, bonding group, ring structure, and right side terminal group, according to the definitions shown in Table 1 below. Compound No. added to the compounds of the present invention shown in the Composition Examples is to indicate that the compounds to which the same Compound No. is added both in the Composition Examples and Examples described below are the same ones.

In the Composition Examples and Examples, "%" means "% by weight" unless otherwise indicated. Data of physical properties of liquid crystal composition in Composition Examples are indicated by TNI (N-I transition point or clearing point: ° C.), η (viscosity: determination temperature 20° C.), Δn (optical anisotropy value: determination temperature 25° C.), Δε (dielectric anisotropy value: determination temperature 25° C.), and Vth (threshold voltage: determination temperature 25° C.).

TABLE 1

Method for Designating Compounds Using Symbols
R—(A$_1$)—Z$_1$—...—Z$_n$—(A$_n$)—X

| 1) Left side terminal group R— | Symbol |
|---|---|
| C$_n$H$_{2n+1}$— | n- |
| C$_n$H$_{2n+1}$CH=CHC$_m$H$_{2m}$— | nVm- |
| C$_n$H$_{2n+1}$OC$_m$H$_{2m}$— | nOm- |
| CH$_2$=CHC$_n$H$_{2n}$— | Vn- |
| CH$_2$=CH— | V— |
| C$_n$H$_{2n+1}$CH=CH— | nV— |
| F—C$_n$H$_{2n}$— | Fn- |
| CH$_2$=CHC$_2$H$_4$CH=CH— | V2V— |

| 2) Ring structure —(A$_1$)—, —(A$_n$)— | Symbol |
|---|---|
| 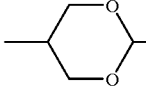 | D |
| 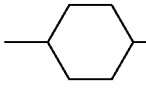 | H |
| 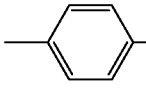 | B |
| 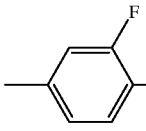 | B(F) |
| 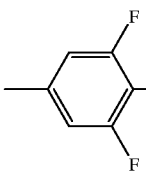 | B(F, F) |

TABLE 1-continued

Method for Designating Compounds Using Symbols
R—(A$_1$)—Z$_1$—...—Z$_n$—(A$_n$)—X

| | Symbol |
|---|---|
| 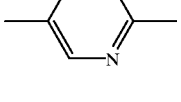 | Py |
| 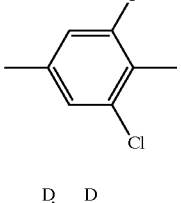 | B(F, CL) |
| 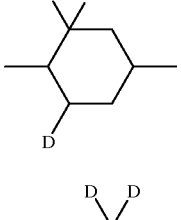 | H(1D, 2D, 3D) |
| 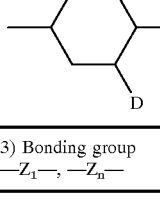 | H((5D, 6D, 7D) |

| 3) Bonding group —Z$_1$—, —Z$_n$— | Symbol |
|---|---|
| —C$_2$H$_4$— | 2 |
| —COO— | E |
| —C≡C— | T |
| —CH=CH— | V |
| —CF$_2$O— | CF2O |

| 4) Right side terminal group —X | Symbol |
|---|---|
| —CN | —C |
| —OC$_n$H$_{2n+1}$ | —On |
| —F | —F |
| —C$_n$H$_{2n+1}$ | -n |
| —CH=CF$_2$ | —VFF |
| —C$_n$H$_{2n}$CH=CF$_2$ | -nVFF |
| —C$_n$H$_{2n}$CH=CH$_2$ | -nV |
| —C$_n$H$_{2n}$CH=CHC$_m$H$_{2m+1}$ | -nVm |
| —OCF$_2$H | —OCF2H |
| —OCF$_3$ | —OCF3 |
| —Cl | —CL |
| —OCF$_2$CF$_2$H | —OCF2CF2H |
| —OCF$_2$CFHCF$_3$ | —OCF2CFHCF3 |
| —CF$_3$ | —CF3 |
| —C≡C—CN | —TC |
| —CH=CHC$_2$H$_4$—F | —V2F |

5) Examples of Designation

Example 1    3-H2B(F,F)B(F)—F

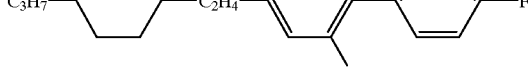

TABLE 1-continued

Method for Designating Compounds Using Symbols
R—(A₁)—Z₁—...—Zₙ—(Aₙ)—X

Example 2    1V2-BEB(F,F)—C

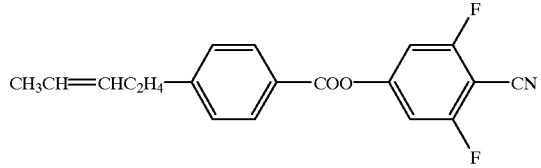

Composition Example 1

| | |
|---|---|
| 5-pyB(F,F)B(F)-OCF3 (No. 17) | 14.0% |
| 1V2-BEB(F,F)-C | 5.0% |
| 3-HB-C | 25.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |
| 3-HB(F)TB-2 | 6.0% |

TNI = 76.7 (° C.)
Δn = 0.151
Δε = 11.4
Vth = 1.90 (V)

Liquid crystal composition prepared by adding 0.8 part by weight of optically active compound (Op-4) to 100 parts by weight of the composition described above had a pitch of 10.5 μm.

Composition Example 2

| | |
|---|---|
| 5-PyB(F)B(F,F)-F (No. 1) | 5.0% |
| 3-PyB(F,CL)B-CL (No. 19) | 5.0% |
| 4-B(F,F)PyB(F)-OCF2CF2H (No. 37) | 5.0% |
| 2O1-BEB(F)-C | 5.0% |
| 3O1-BEB(F)-C | 15.0% |
| 4O1-BEB(F)-C | 13.0% |
| 5O1-BEB(F)-C | 13.0% |
| 2-HHB(F)-C | 15.0% |
| 3-HB(F)TB-2 | 4.0% |
| 3-HB(F)TB-3 | 4.0% |
| 3-HB(F)TB-4 | 4.0% |
| 3-HHB-1 | 8.0% |
| 3-HHB-O1 | 4.0% |

Composition Example 3

| | |
|---|---|
| 3-B(F)B(F)PyB-F (No. 135) | 5.0% |
| 5-PyB(F)EB(F,F)-F (No. 41) | 6.0% |
| 3-BEB(F)-C | 8.0% |
| 3-HB-C | 8.0% |
| V-HB-C | 8.0% |
| 1V-HB-C | 8.0% |
| 3-HB-O2 | 3.0% |
| 3-HH-2V | 14.0% |
| 3-HH-2V1 | 7.0% |
| V2-HHB-1 | 15.0% |
| 3-HHB-1 | 5.0% |
| 3-HHEB-F | 7.0% |
| 3-H2BTB-2 | 6.0% |

Composition Example 4

| | |
|---|---|
| 4-BpyB(F,F)B(F)-F (No. 142) | 2.0% |
| 7-B(F)PyB(F)-CF3 (No. 26) | 2.0% |
| V2-HB-C | 12.0% |
| 1V2-HB-C | 12.0% |
| 3-HB-C | 15.0% |
| 3-H(1D,2D,3D)B-C | 9.0% |
| 3-HB(F)-C | 5.0% |
| 2-BTB-1 | 2.0% |
| 3-HH-4 | 8.0% |
| 3-HH-VFF | 6.0% |
| 2-H(1D,2D,3D)HB-C | 3.0% |
| 3-HHB-C | 6.0% |
| 3-HB(F)TB-2 | 8.0% |
| 3-H2BTB-2 | 5.0% |
| 3-H2BTB-3 | 5.0% |

Composition Example 5

| | |
|---|---|
| 4-HPyB(F)B(F)-F (No. 150) | 3.0% |
| 2-PyB(F,F)CF2OB(F)-F (No. 74) | 2.0% |
| 3-PyEB(F,F)B(F,F)-OCF3 (No. 92) | 2.0% |
| 1-PyCF2OB(F)B-F (No. 108) | 2.0% |
| 5-BEB(G)-C | 5.0% |
| V-HB-C | 11.0% |
| 5-PyB-C | 6.0% |
| 4-BB-3 | 11.0% |
| 3-HH-2V | 10.0% |
| 5-HH-V | 11.0% |
| V-HHB-1 | 7.0% |
| V2-HHB-1 | 15.0% |
| 1V2-HBB-2 | 10.0% |
| 3-HHEBH-3 | 5.0% |

Composition Example 6

| | |
|---|---|
| 5-PyB(F,F)B(F,F)EB(F)-OCF2CFHCF3 (No. 156) | 4.0% |
| 5-PyB(F,F)B(F,F)B(F)-CL (No. 129) | 4.0% |
| 1V2-BEB(F,F)-C | 8.0% |
| 3-HB-C | 10.0% |
| V2V-HB-C | 14.0% |
| V2V-HH-3 | 19.0% |
| 3-HB-O2 | 4.0% |
| 3-HHB-1 | 10.0% |
| 3-HHB-3 | 15.0% |
| 3-HB(F)TB-2 | 4.0% |
| 3-HB(F)TB-3 | 4.0% |
| 3-H2BTB-2 | 4.0% |

Composition Example 7

| | |
|---|---|
| F5-PyB(F,F)B(F)-F (No. 10) | 6.0% |
| V2-HB-TC | 10.0% |
| 3-HB-TC | 10.0% |
| 3-HB-C | 10.0% |
| 5-HB-C | 7.0% |

Composition Example 8

| | |
|---|---|
| 5-BB-C | 3.0% |
| 2-BTB-1 | 10.0% |
| 2-BTB-O1 | 5.0% |
| 3-HH-4 | 5.0% |
| 3-HHB-1 | 10.0% |
| 3-HHB-3 | 11.0% |
| 3-H2BTB-2 | 3.0% |
| 5-BTB(F)TB-3 | 10.0% |

Composition Example 8

| | | |
|---|---|---|
| 5-PyB(F,F)B(F)-OCF3 (No. 17) | | 8.0% |
| 1V2-BEB(F,F)-C | | 6.0% |
| 3-HB-C | | 18.0% |
| 2-BTB-1 | | 10.0% |
| 5-HH-VFF | | 30.0% |
| 1-BHH-VFF | | 8.0% |
| 1-BHH-2VFF | | 11.0% |
| 3-H2BTB-2 | | 5.0% |
| 3-HHB-1 | | 4.0% |

TNI = 73.1 (° C.)
Δn = 0.124
Δε = 9.0
Vth = 1.73 (V)

Composition Example 9

| | |
|---|---|
| 5-PyB(F,F)B(F)-OCF3 (No. 17) | 13.0% |
| 2-HHB(F)-F | 17.0% |
| 3-HHB(F)-F | 17.0% |
| 5-HHB(F)-F | 16.0% |
| 2-H2HB(F)-F | 10.0% |
| 3-H2HB(F)-F | 5.0% |
| 5-H2HB(F)-F | 10.0% |
| 2-HBB(F)-F | 6.0% |
| 3-HBB(F)-F | 6.0% |

TNI = 94.5 (° C.)
Δn = 0.098
Δε = 8.1
Vth = 1.82 (V)

Liquid crystal composition prepared by adding 0.3 part by weight of optically active compound (Op-8) to 100 parts by weight of the composition described above had a pitch of 79.0 μm.

Composition Example 10

| | |
|---|---|
| 5-PyB(F)B(F,F)-F (No. 1) | 4.0% |
| 3-HB-CL | 10.0% |
| 5-HB-CL | 4.0% |
| 7-HB-CL | 4.0% |
| 1O1-HH-5 | 5.0% |
| 2-HBB(F)-F | 8.0% |
| 3-HBB(F)-F | 8.0% |
| 5-HBB(F)-F | 14.0% |
| 4-HHB-CL | 8.0% |
| 5-HHB-CL | 8.0% |
| 3-H2HB(F)-CL | 4.0% |
| 3-HBB(F,F)-F | 10.0% |
| 5-H2BB(F,F)-F | 9.0% |
| 3-HB(F)VB-2 | 4.0% |

Composition Example 11

| | | |
|---|---|---|
| 3-PyB(F,CL)B-CL | (No. 19) | 5.0% |
| 4-B(F,F)PyB(F)-OCF2CF2H | (No. 37) | 5.0% |
| 7-B(F)PyB(F)-CF3 | (No. 26) | 5.0% |
| 5-PyB(F)EB(F,F)-F | (No. 41) | 5.0% |
| 3-HHB(F,F)-F | | 9.0% |
| 3-H2HB(F,F)-F | | 8.0% |
| 4-H2HB(F,F)-F | | 8.0% |
| 5-H2HB(F,F)-F | | 8.0% |
| 3-HBB(F,F)-F | | 21.0% |
| 3-H2BB(F,F)-F | | 10.0% |
| 5-HHBB(F,F)-F | | 3.0% |
| 5-HHEBB-F | | 2.0% |
| 3-HH2BB(F,F)-F | | 3.0% |
| 1O1-HBBH-4 | | 4.0% |
| 1O1-HBBH-5 | | 4.0% |

Composition Example 12

| | | |
|---|---|---|
| 2-PyB(F,F)CF2OB(F)-F | (No. 74) | 5.0% |
| 3-PyEB(F,F)B(F,F)-OCF3 | (No. 92) | 4.0% |
| 1-PyCF2OB(F)B-F | (No. 10) | 4.0% |
| 5-PyB(F,F)B(F,F)B(F)-CL | (No. 129) | 4.0% |
| 3-B(F)B(F)PyB-F | (No. 135) | 4.0% |
| 5-HB-F | | 12.0% |
| 6-HB-F | | 9.0% |
| 7-HB-F | | 7.0% |
| 5-HHB-OCF3 | | 5.0% |
| 3-HH2B-OCF3 | | 4.0% |
| 5-HH2B-OCF3 | | 4.0% |
| 3-HHB(F,F)-OCF3 | | 5.0% |
| 3-HBB(F)-F | | 10.0% |
| 5-HBB(F)-F | | 10.0% |
| 3-HH2B(F)-F | | 3.0% |
| 3-HB(F)BH-3 | | 3.0% |
| 5-HBBH-3 | | 3.0% |
| 3-HHB(F,F)-OCF2H | | 4.0% |

Composition Example 13

| | | |
|---|---|---|
| 4-BPyB(F,F)B(F)-F | (No. 142) | 3.0% |
| 4-HPyB(F)B(F)-F | (No. 150) | 3.0% |
| 3-H2HB(F,F)-F | | 7.0% |
| 5-H2HB(F,F)-F | | 8.0% |
| 3-HHB(F,F)-F | | 10.0% |
| 4-HHB(F,F)-F | | 5.0% |
| 3-HH2B(F,F)-F | | 9.0% |
| 5-HH2B(F,F)-F | | 9.0% |
| 3-HBB(F,F)-F | | 15.0% |
| 5-HBB(F,F)-F | | 15.0% |
| 3-HBEB(F,F)-F | | 2.0% |
| 4-HBEB(F,F)-F | | 2.0% |
| 5-HBEB(F,F)-F | | 2.0% |
| 3-HHEB(F,F)-F | | 10.0% |

Composition Example 14

| | | |
|---|---|---|
| F5-PyB(F,F)B(F)-F | (No. 10) | 8.0% |
| 5-PyB(F,F)B(F,F)EB(F)OCF2CFHCF3 | (No. 156) | 4.0% |
| 7-HB(F)-F | | 5.0% |
| 5-H2B(F)-F | | 5.0% |
| 3-HB-O2 | | 10.0% |
| 3-HH-4 | | 2.0% |
| 3-HH(5D,6D,7D)-4 | | 3.0% |

-continued

| | |
|---|---|
| 2-HHB(F)-F | 10.0% |
| 3-HHB(F)-F | 10.0% |
| 5-HH(5D,6D,7D)B(F)F | 10.0% |
| 3-H2HB(F)-F | 5.0% |
| 2-HBB(F)-F | 3.0% |
| 3-HBB(F)-F | 3.0% |
| 5-HBB(F)-F | 6.0% |
| 2-H2BB(F)-F | 5.0% |
| 3-H2BB(F)-F | 6.0% |
| 3-HHB-O1 | 5.0% |

Composition Example 15

| | | |
|---|---|---|
| 5-PyB(F,F)B(F)-OCF3 | (N. 17) | 12.0% |
| 7-HB(F,F)-F | | 3.0% |
| 3-H2HB(F,F)-F | | 12.0% |
| 4-H2HB(F,F)-F | | 10.0% |
| 5-H2HB(F,F)-F | | 10.0% |
| 3-HHB(F,F)-F | | 5.0% |
| 4-HHB(F,F)-F | | 5.0% |
| 3-HH2B(F,F)-F | | 15.0% |
| 5-HH2B(F,F)-F | | 10.0% |
| 3-HBB(F,F)-F | | 12.0% |
| 3-HBCF2OB(F,F)-F | | 6.0% |
| TNI = 71.9 (° C.) | | |
| Δn = 0.092 | | |
| Δε = 11.1 | | |
| Vth = 1.43 (V) | | |

Liquid crystal composition prepared by adding 0.25 part by weight of optically active compound (Op-5) to 100 parts by weight of the composition described above had a pitch of 63.0 μm.

Composition Example 16

| | | |
|---|---|---|
| 5-PyB(F,F)B(F)-OCF3 | (No. 17) | 10.0% |
| 7-HB(F,F)-F | | 5.0% |
| 3-H2HB(F,F)-F | | 12.0% |
| 4-H2HB(F,F)-F | | 10.0% |
| 3-HHB(F,F)-F | | 10.0% |
| 4-HHB(F,F)-F | | 5.0% |
| 3-HBB(F,F)-F | | 10.0% |
| 4-HHEB(F,F)-F | | 3.0% |
| 5-HHEB(F,F)-F | | 3.0% |
| 2-HBEB(F,F)-F | | 3.0% |
| 3-HBEB(F,F)-F | | 5.0% |
| 5-HBEB(F,F)-F | | 3.0% |
| 3-HDB(F,F)-F | | 15.0% |
| 3-HHBB(F,F)-F | | 6.0% |
| TNI = 70.9 (° C.) | | |
| Δn = 0.093 | | |
| Δε = 15.1 | | |
| Vth = 1.29 (V) | | |

Composition Example 17

| | | |
|---|---|---|
| 5-PyB(F,F)B(F)-OCF3 | (No. 17) | 5.0% |
| 5-PyB(F)B(F,F)-F | (No. 1) | 5.0% |
| 5-H4HB(F,F)-F | | 7.0% |
| 5-H4HB-OCF3 | | 15.0% |
| 3-H4HB(F,F)-CF3 | | 8.0% |
| 3-HB-CL | | 6.0% |
| 5-HB-CL | | 4.0% |

-continued

| | |
|---|---|
| 2-H2BB(F)-F | 5.0% |
| 3-H2BB(F)-F | 10.0% |
| 5-HVHB(F,F)-F | 5.0% |
| 3-HHB-OCF3 | 5.0% |
| 3-H2HB-OCF3 | 5.0% |
| V-HHB(F)-F | 5.0% |
| 3-HHB(F)-F | 5.0% |
| 5-HHEB-OCF3 | 2.0% |
| 3-HBEB(F,F)-F | 5.0% |
| 5-HH-V2F | 3.0% |

Composition Example 18

| | | |
|---|---|---|
| 5-PyB(F,F)B(F)-OCF3 | (No. 17) | 8.0% |
| 5-HB-CL | | 12.0% |
| 3-HH-4 | | 7.0% |
| 3-HB-O2 | | 20.0% |
| 3-H2HB(F,F)-F | | 8.0% |
| 3-HBB(F,F)-F | | 6.0% |
| 2-HHB(F)-F | | 5.0% |
| 3-HHB(F)-F | | 5.0% |
| 5-HHB(F)-F | | 5.0% |
| 2-H2HB(F)-F | | 2.0% |
| 3-H2HB(F)-F | | 1.0% |
| 5-H2HB(F)-F | | 2.0% |
| 3-HHBB(F,F)-F | | 4.0% |
| 3-HBCF2OB-OCF3 | | 4.0% |
| 5-HBCF2OB(F,F)-CF3 | | 4.0% |
| 3-HHB-1 | | 3.0% |
| 3-HHB-O1 | | 4.0% |
| TNI = 69.6 (° C.) | | |
| Δn = 0.093 | | |
| Δε = 5.8 | | |
| Vth = 1.99 (V) | | |

EXAMPLES

Now, the present invention will be described in more detail with reference to Examples. In the Examples, Cr indicates crystal, $S_A$: smectic A phase, N: nematic phase, and I: isotropic liquid phase.

Example 1

Preparation of 2-(4-(3-fluoro-4-trifluoromethoxyphenyl)-3,5-difluorophenyl)-5-pentylpyrimidine (Compound expressed by the general formula (1) wherein R is pentyl group, n1 is 0, n2 is 1, ring B is (a), Za, Zb, and Zc are single bond, $Q_1$, $Q_3$, $Q_4$, $Q_6$, and $Q_7$ are hydrogen atom, $Q_2$ and $Q_5$ are fluorine atom, and Y is $OCF_3$
(Compound No. 17))

(First stage)

In 18.74 kg of dimethyl formamide (DMF) was added 11.48 kg of phosphorus oxychloride at 10° C., and stirred at the same temperature for 1 hour. To the sticky solution thus obtained was added 25 l of a solution of 6.0 kg (31.9 mol) of 1,1-diethoxyheptane in dichloromethane at 10° C., stirred at the same temperature for 2 hours, and then heated up to 70° C. in 30 min. The reaction solution was cooled down, gradually added to an aqueous solution of 33.2 kg of potassium carbonate and 100 l of water so that the temperature did not exceed 30° C., and then stirred at room temperature for 5 hours. The product was extracted with chloroform. The extract was washed with saturated aqueous solution of sodium chloride, and dried over anhydrous magnesium sulfate. The solvent was distilled off under a reduced pressure, and the residue was purified by distillation to obtain 2.6 kg (15.3mol) of 2-ethoxymethylidenylheptanal. Yield of this product was 48%.

(Second stage)

In 1 l of ethanol were stirred 1197 g (7.03 mol) of the 2-ethoxymethylidenylheptanal described above and 507 g (8.44 mol) of urea for 5 min, nd the mixture was cooled down to 0° C. Subsequently, 1 l of 12N-hydrochloric acid was added dropwise to the mixture, and the suspension thus resulted was heated to reflux for 6 hours.

The reaction solution was cooled down and neutralized with 2N aqueous solution of sodium hydroxide. The product was extracted with chloroform, and the extract was washed with water, and dried over anhydrous magnesium sulfate. The solvent was distilled off under a reduced pressure, and the residue was recrystallized from toluene to obtain 972 g (5.8 mol) of 2-hydroxy-5-pentylpyrimidine. Yield of this product from 2-ethoxymethylidenylheptanal was 83%.

(Third stage)

In 500 ml of phosphorus oxychloride was added 120.4 g (0.724 mol) of the 2-hydroxy-5-pentylpyrimidine described above, and heated to reflux for 5 hours. Excess amount of phosphorus oxychloride was distilled off under a reduced pressure, and the residue was added into an ice water. The product was extracted with toluene, and the extract was washed with aqueous solution of 2N aqueous solution of sodium hydroxide and water in turn, and dried over anhydrous magnesium sulfate. The solvent was distilled off under a reduced pressure. The residue was purified by distillation to obtain 76.3 g (0.413 mol) of 2-chloro-5-pentylpyrimidine. Yield of this product was 57%.

(Fourth stage)

Grignard reagent was prepared from dried magnesium and 49.0 g (254 mmol) of 3,5-difluorobromobenzene in 200 ml of tetrahydrofuran (THF), 1 g of NiCl$_2$ (dppp) was added thereto, 36.0 g (195 mmol) of the 2-chloro-5-pentylpyrimidine described above was added dropwise thereto, and the product was heated to reflux for 2 hours. The reaction solution was cooled down, and added into 200 ml of 1N-hydrochloric acid. The product was extracted with ether, and the extract was washed with saturated aqueous solution of sodium bicarbonate and water in turn, and then dried over anhydrous magnesium sulfate. The solvent was distilled off under a reduced pressure. The residue was purified by silica gel column chromatography (eluent: heptane/toluene=1/1) to obtain 8.0 g (30 mmol) of 2-(3,5-difluorophenyl)-5-pentylpyrimidine. Yield of this product was 15%.

(Fifth stage)

In 80 ml of THF was dissolved 8.0 g (30 mmol) of the 2-(3,5-difluorophenyl)-5-pentylpyrimidine described above, and cooled down to −60° C. under nitrogen gas atmosphere. To this solution was added dropwise 20 ml of 1.60 M solution of n-butyl lithium (32 mmol) in hexane while maintaining the condition that the temperature of the solution did not exceed −50° C., and then stirred at the same temperature for 1 hour. Subsequently, 64 ml of 0.5 M solution of zinc chloride (32 mmol) in THF was added dropwise to the reaction solution while maintaining the condition that the temperature of the solution did not exceed −50° C., warmed up to room temperature, and then stirred for 30 min. To this solution were added 0.5 g of tetrakistriphenylphosphine palladium and 8.3 g of 3-fluoro-4-trifluoromethoxybromobenzene, and heated to reflux for 3 hours. To the reaction solution was added 100 ml of water, and the product was extracted with toluene. The extract was washed with 3N-hydrochloric acid, saturated aqueous solution of sodium bicarbonate, and saturated aqueous solution of sodium chloride in turn, and dried over anhydrous magnesium sulfate. The solvent was distilled off. The residue was purified by silica gel column chromatography (eluent: heptane/toluene=1/1), and then recrystallized twice from heptane/ethyl acetate=1/1 to obtain 0.09 g (0.2 mmol) of 2-(4-(3-fluoro-4-trifluoromethoxyphenyl)-3,5-difluorophenyl)-5-pentylpyrimidine. Yield of this product from 2-(3,5-difluorophenyl)-5-pentylpyrimidine was 0.7%.

1H-NMR (CDCl$_3$) δ (ppm): 8.65 (s, 2H), 8.21~7.98 (m, 2H), 7.50~7.36 (m, 3H), 2.66 (t, 2H), 1.79~1.27 (m, 6H), 0.92 (t, 3H).

C-C$_A$ point 66.9° C., S$_A$-I point 82.1° C.

Following compounds (Compound Nos. 1 to 170) can be prepared according to the descriptions in the foregoing including Example 1. Compound of Example 1 is shown again below.

No. 1
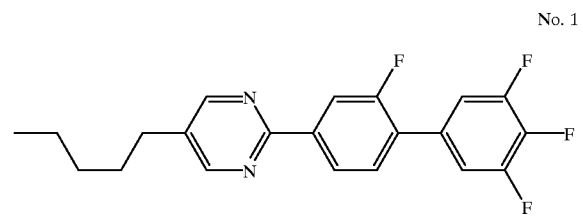

No. 2
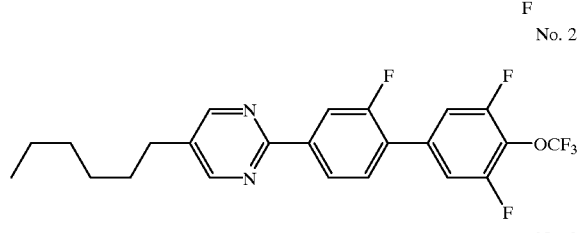

No. 3
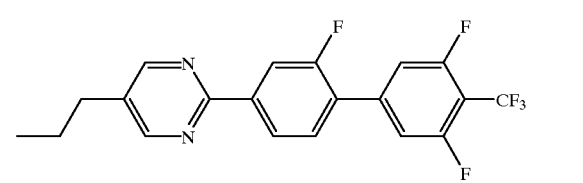

No. 4
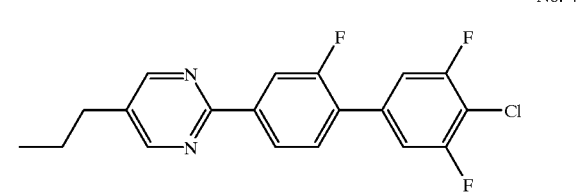

No. 5
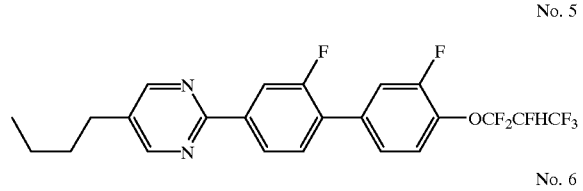

No. 6
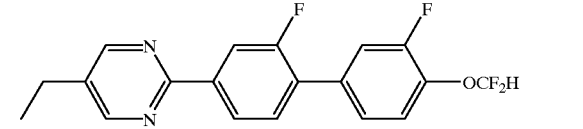

No. 7
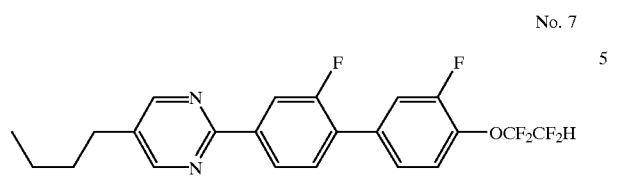
No. 8
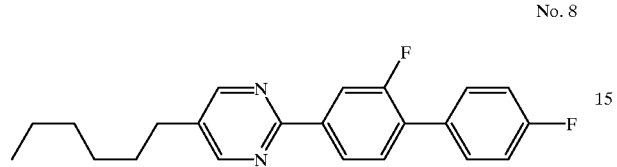
No. 9
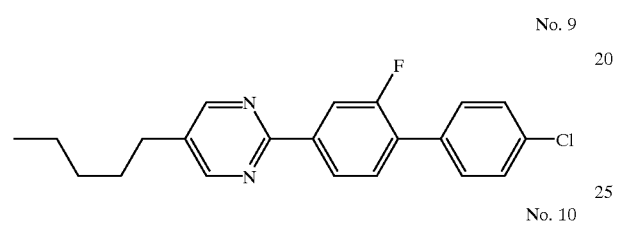
No. 10
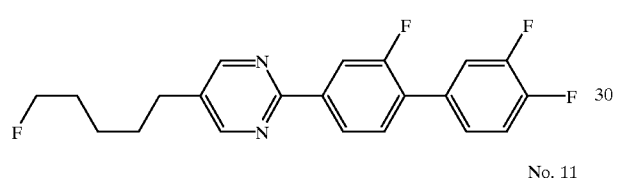
No. 11
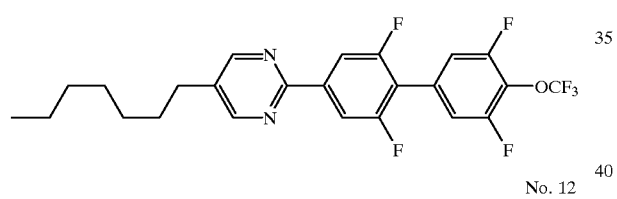
No. 12
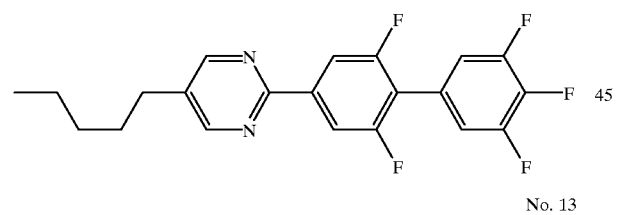
No. 13
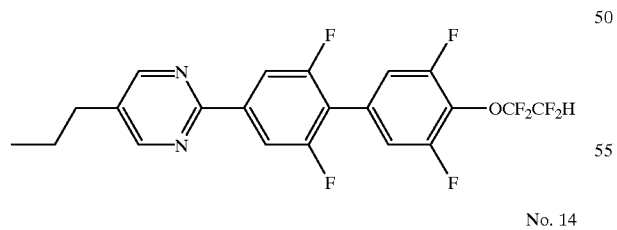
No. 14
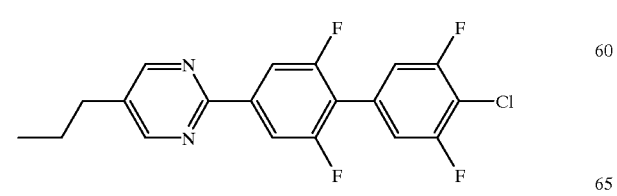
No. 15
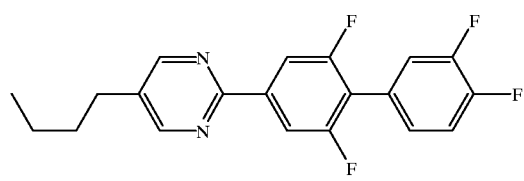
No. 16
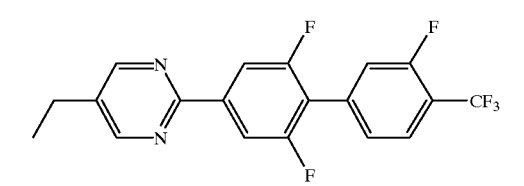
No. 17
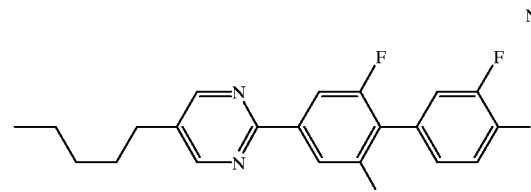
No. 18
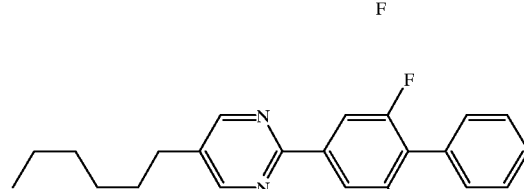
No. 19
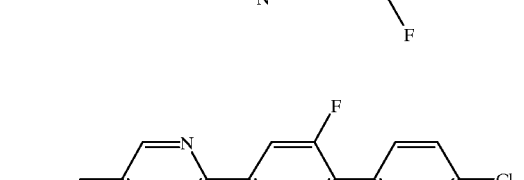
No. 20
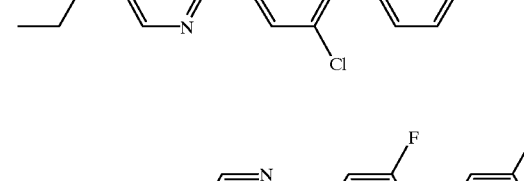
No. 21
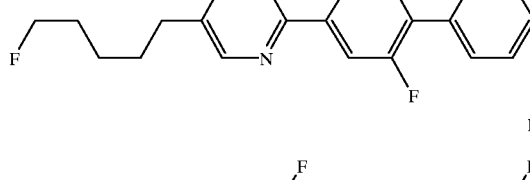
No. 22
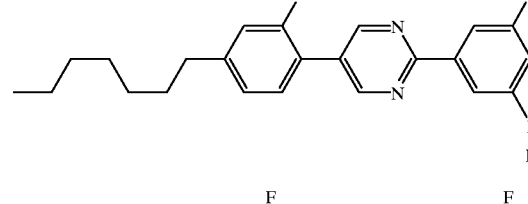

-continued
No. 23
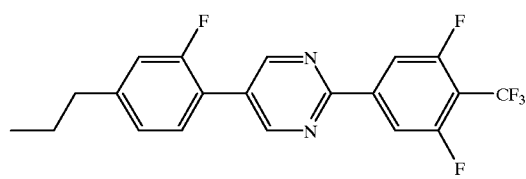
No. 24
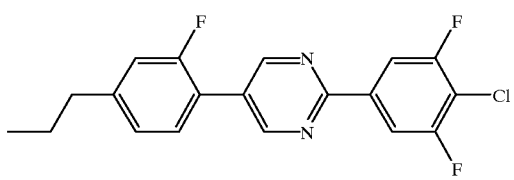
No. 25
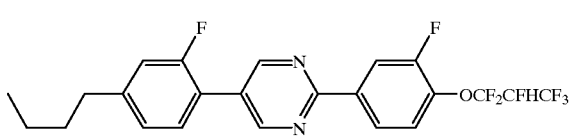
No. 26
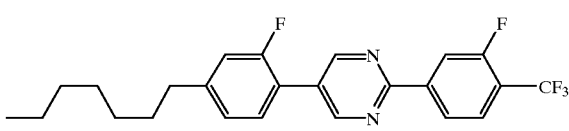
No. 27
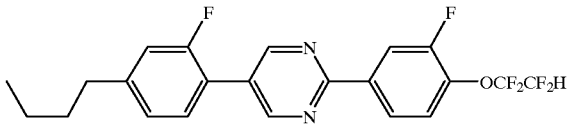
No. 28
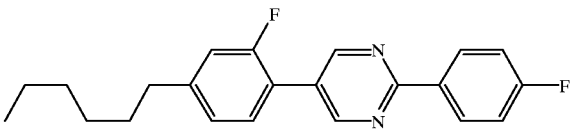
No. 29
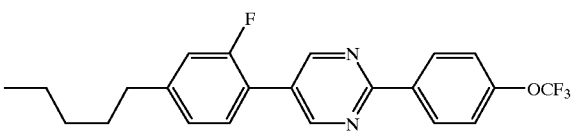
No. 30
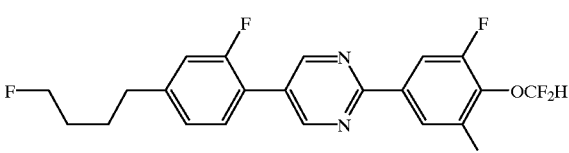
No. 31
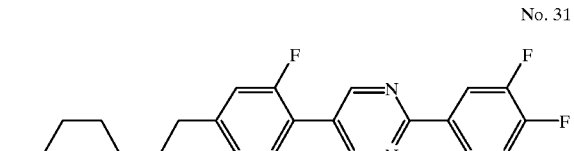
-continued
No. 32
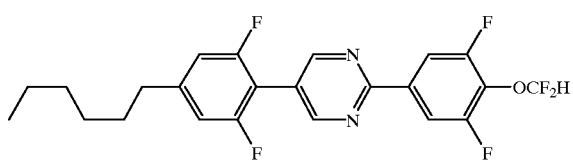
No. 33
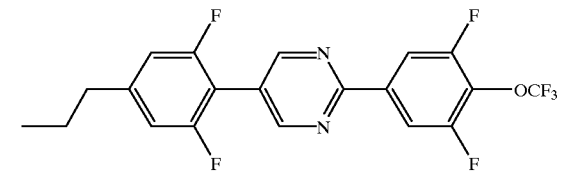
No. 34
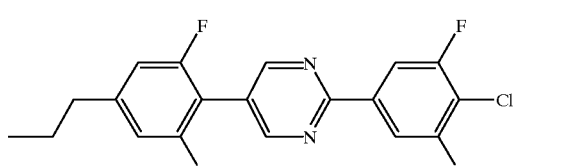
No. 35
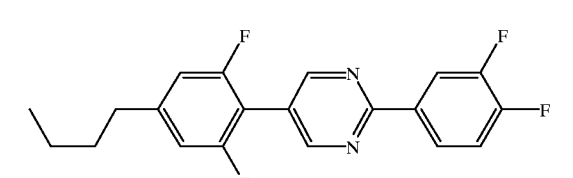
No. 36
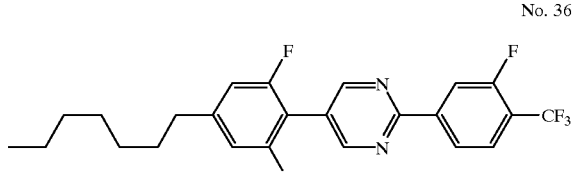
No. 37
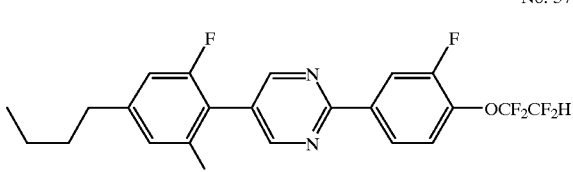
No. 38
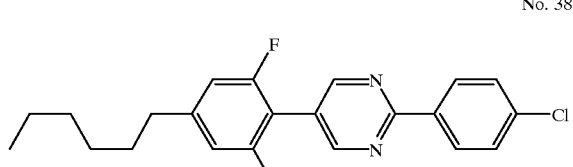
No. 39
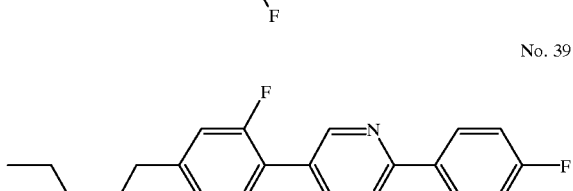

-continued

No. 40

No. 41

No. 42

No. 43

No. 44

No. 45

No. 46

-continued

No. 47

No. 48

No. 49

No. 50

No. 51

No. 52

No. 53

No. 54

No. 55
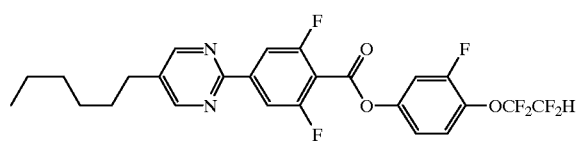
No. 56
No. 57
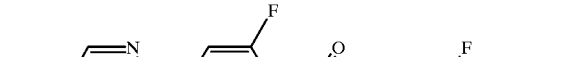
No. 58
No. 59
No. 60
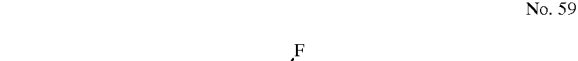
No. 61
No. 62
No. 63
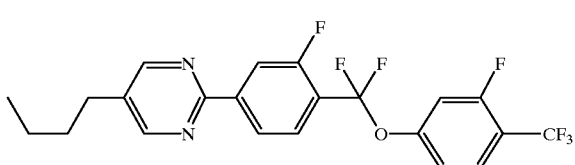
No. 64
No. 65
No. 66
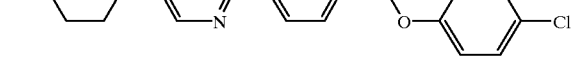
No. 67
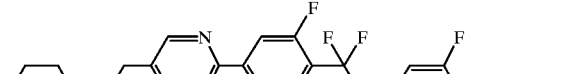
No. 68
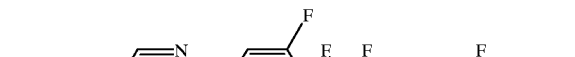
No. 69
No. 70

No. 71
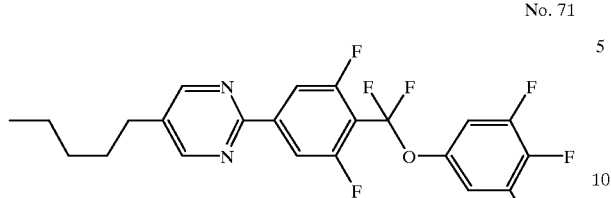
No. 72
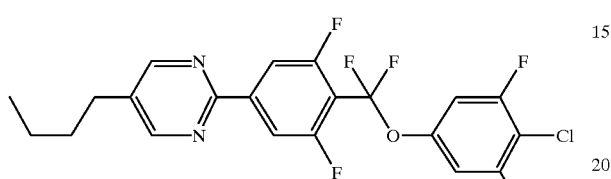
No. 73
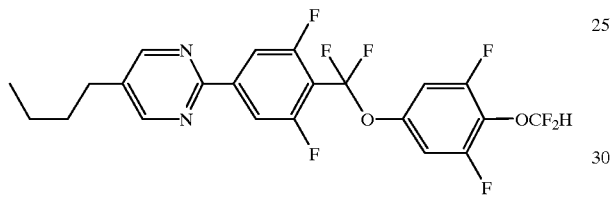
No. 74
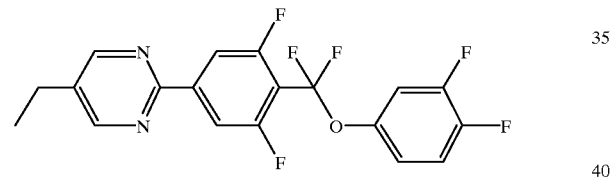
No. 75
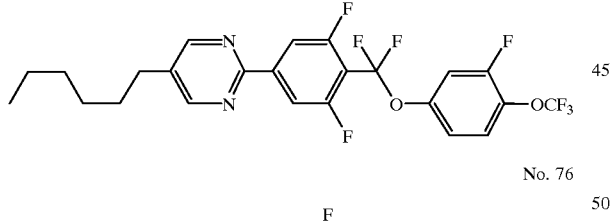
No. 76
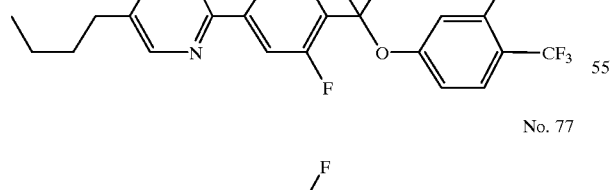
No. 77
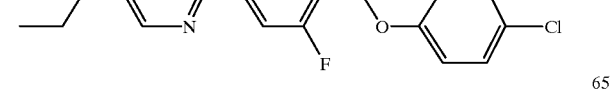
No. 78
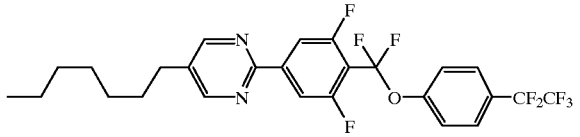
No. 79
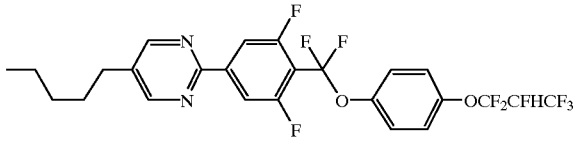
No. 80
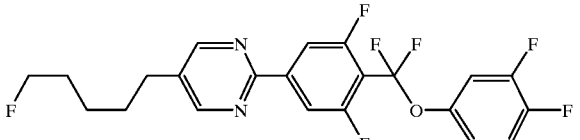
No. 81
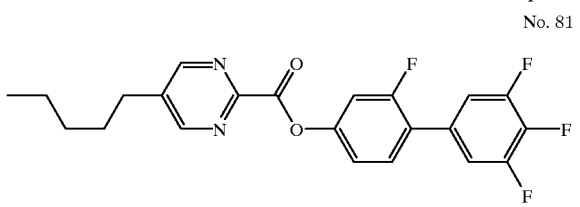
No. 82
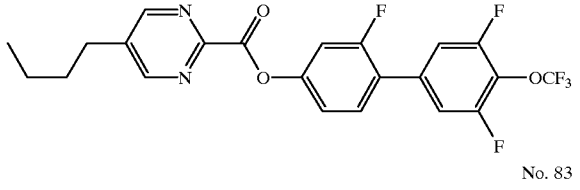
No. 83
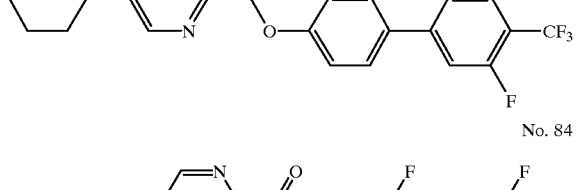
No. 84
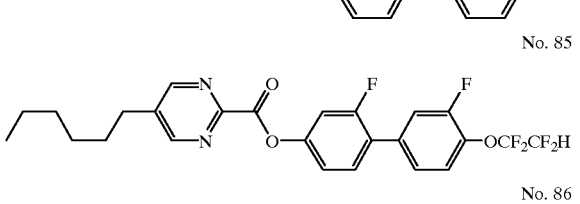
No. 85
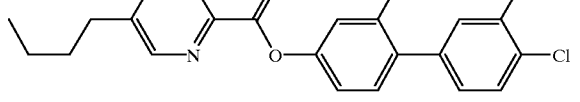
No. 86

-continued

No. 87–No. 103: chemical structure diagrams (pyrimidine ester liquid crystal compounds).

-continued
No. 104
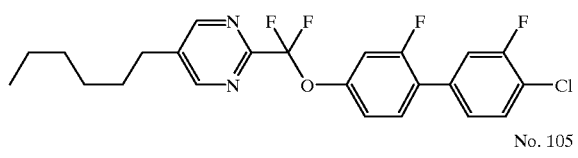
No. 105
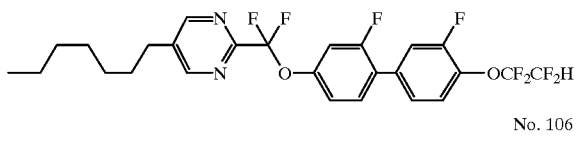
No. 106
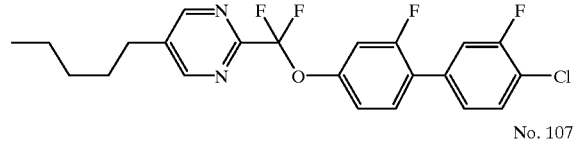
No. 107
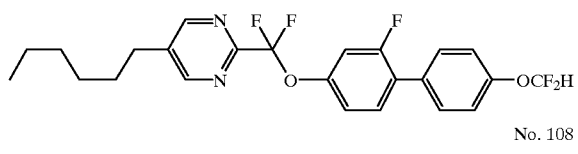
No. 108
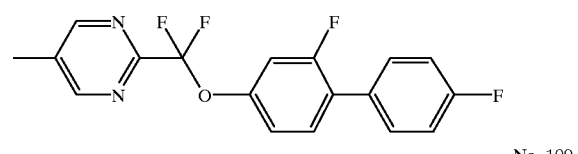
No. 109
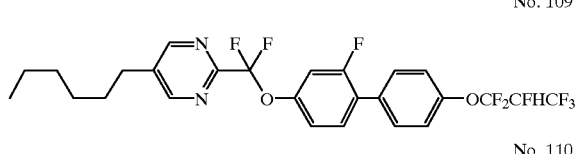
No. 110
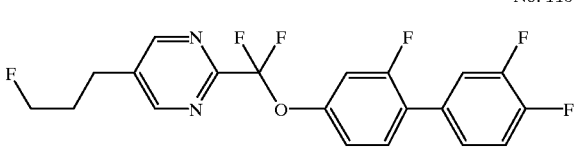
No. 111
No. 112
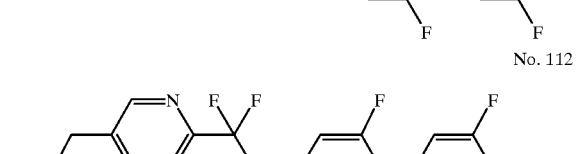
No. 113
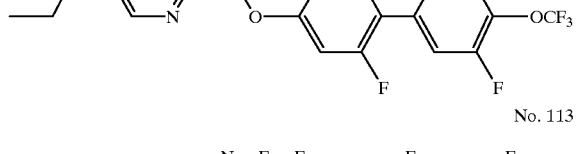
-continued
No. 114
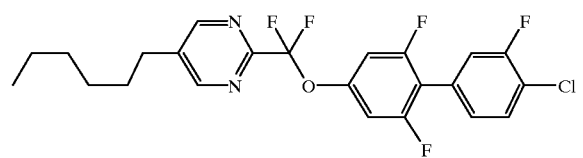
No. 115
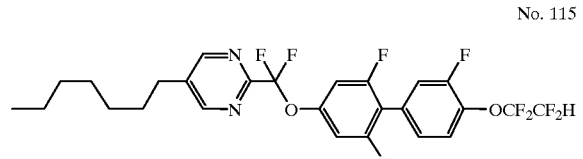
No. 116
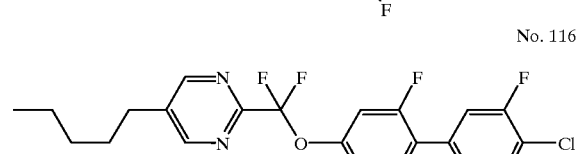
No. 117
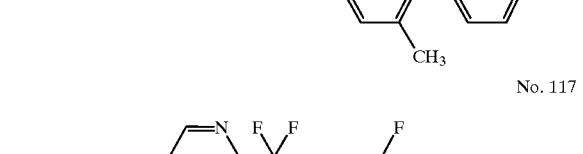
No. 118
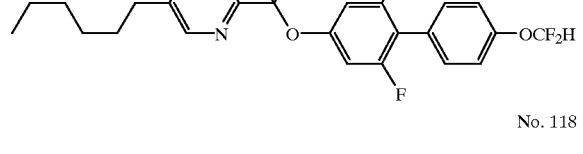
No. 119
No. 120
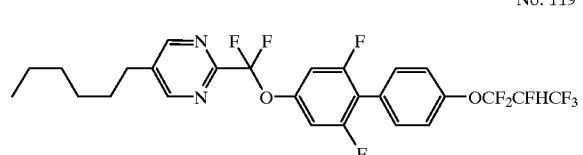
No. 121
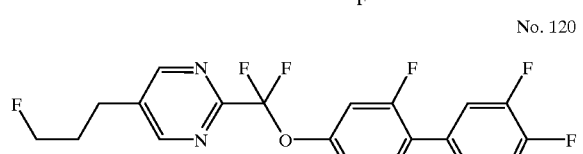
No. 122
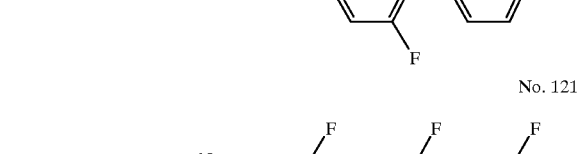

-continued

No. 123
No. 124
No. 125
No. 126
No. 127
No. 128
No. 129
No. 130
No. 131

-continued

No. 132
No. 133
No. 134
No. 135
No. 136
No. 137
No. 138
No. 139
No. 140

-continued
No. 141
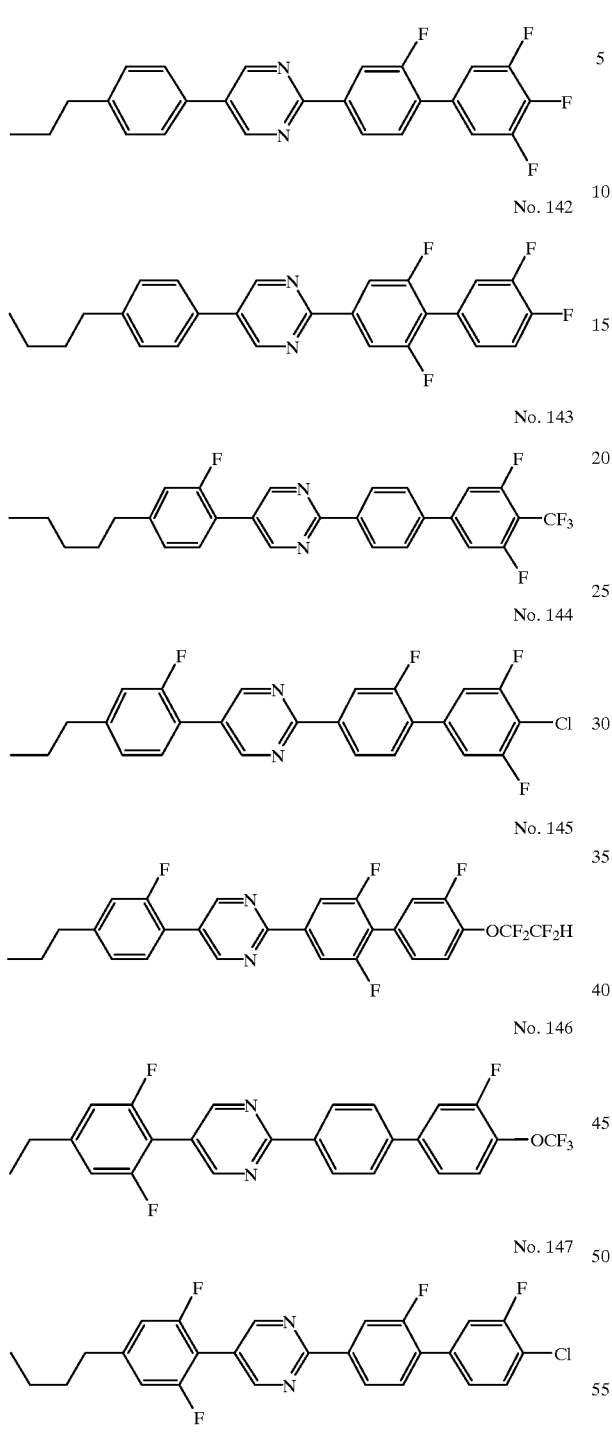
No. 142
No. 143
No. 144
No. 145
No. 146
No. 147
No. 148
-continued
No. 149
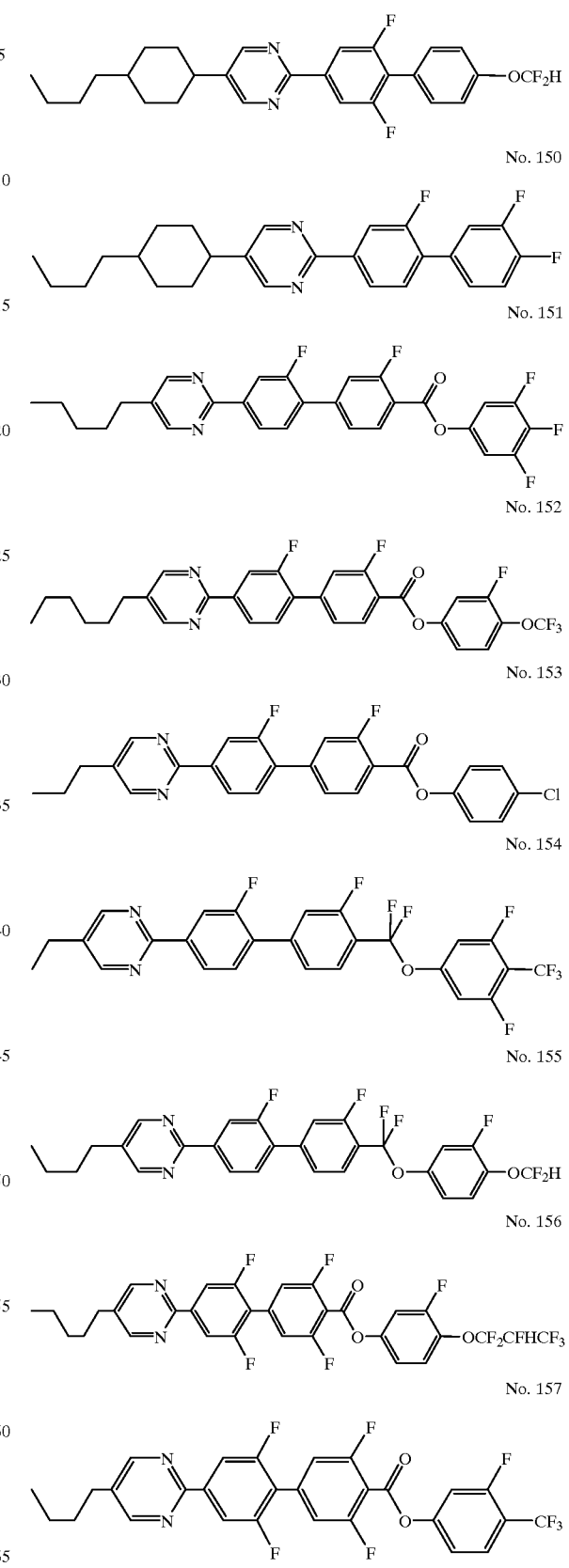
No. 150
No. 151
No. 152
No. 153
No. 154
No. 155
No. 156
No. 157

No. 158
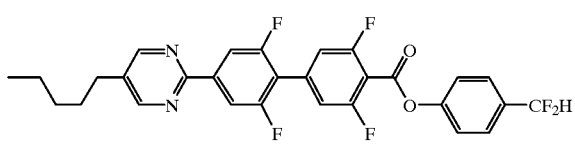

No. 159
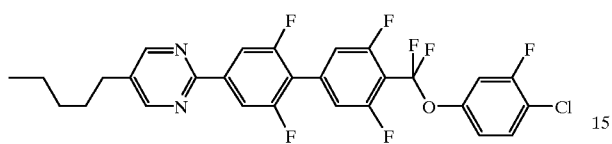

No. 160
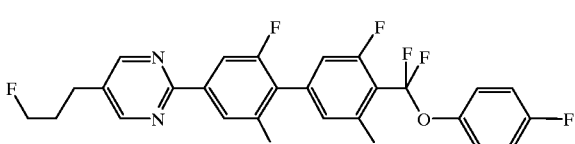

No. 161
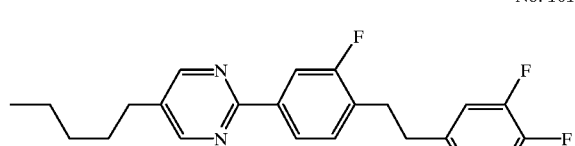

No. 162
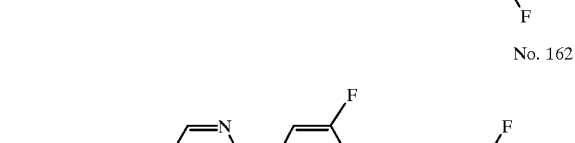

No. 163
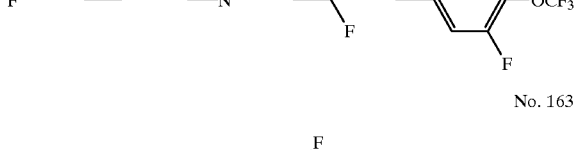

No. 164
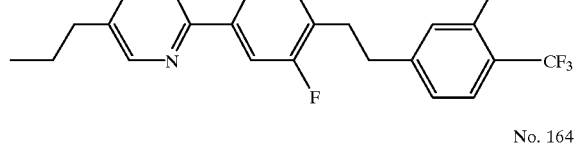

No. 165
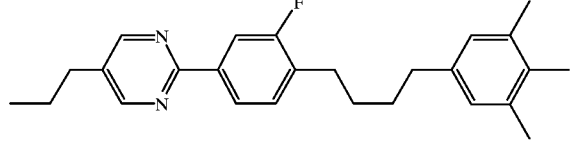

No. 166
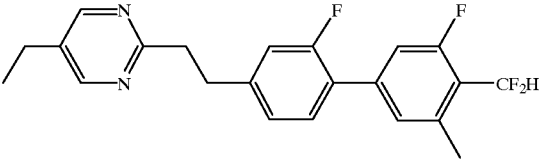

No. 167
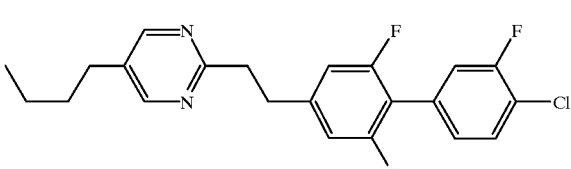

No. 168
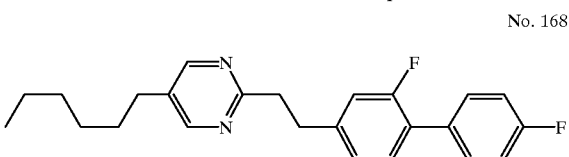

No. 169
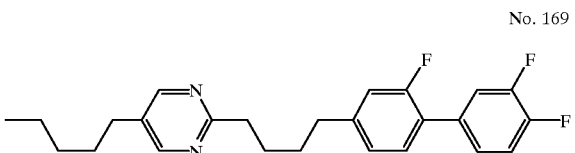

No. 170
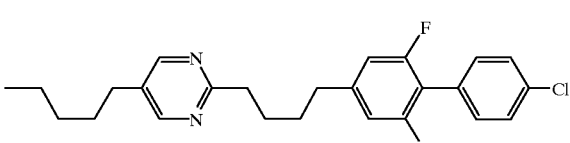

Example 2 (Use Example 1)

Liquid crystal composition (A) comprising
4-(4-propylcyclohexyl)benzonitrile 24%
4-(4-pentylcyclohexyl)benzonitrile 36%
4-(4-heptylcyclohexyl)benzonitrile 25%
4-(4-(4-pentylcyclohexyl)phenyl)benzonitrile 15%
was prepared. This nematic liquid crystal composition had the physical properties as follows:

TNI=71.7 (° C.)
Vth=1.79 (V) (determined at a cell thickness of 9.2 μm)
Δε=11.0
Δn=0.137

Liquid crystal composition (B) was prepared by mixing 15% by weight of the 2-(4-(3-fluoro-4-trifluoromethoxyphenyl)-3,5-difluorophenyl)-5-pentylpyrimidine (Compound No. 17) prepared in Example 1 with 85% by weight of the liquid crystal composition (A). Physical properties of the liquid crystal composition (B) thus obtained were as follows:

TNI=68.2 (° C.)
Vth=1.47 (V) (determined at a cell thickness of 8.9 μm)
Δε=14.0
Δn=0.142

Liquid crystal composition (B) exhibited nematic phase even after it was left at −20° C. for 30 days, and physical properties of the compound (Compound No. 17 described above) calculated by extrapolation from the physical properties and chemical composition of the liquid crystal composition (B) described above were as follows:

TNI=48.4 (° C.)

Δε=31.0

Δn=0.170

Example 3 (Comparative Example 1)

Liquid crystal composition (B-R) comprising 85% by weight of the liquid crystal composition (A) described above and 15% by weight of the 2-(4-(3,4,5-trifluorophenyl)phenyl)-5-pentylpyrimidine (compound of the formula 10) described in Laid-open Japanese Patent Publication No. Hei 2-233626 was prepared. Physical properties of the liquid crystal composition (B-R) were as follows:

TNI=73.5 ° (C)

Vth=1.60 (V) (determined at a cell thickness of 9.3 μm)

Δε=12.3

Δn=0.147

This liquid crystal composition (B-R) separated crystals 5 days after the composition was maintained at −20° C.

Physical properties of the compound (of the formula 10 described above) calculated by extrapolation from the physical properties and chemical composition of the liquid crystal composition (B-R) described above were as follows:

TNI=83.7 (° C.)

Δε=18.7

Δn=0.204

From the results, it can be seen that Compound No. 17 of the present invention is lower in N-I transition point by about 10° C. than the compound of the formula 10, but has about 1.7 times as high Δε as the compound of the formula 10, and that the compound of the present invention is excellent in miscibility with other liquid crystals at low temperatures.

Example 4

Liquid crystal composition (C) comprising 4-(2-(4-ethylcycloyhexyl)ethyl)cyclohexyl-3,4-difluorobenzene 40%

4-(2-(4-propylcycloyhexyl)ethyl)cyclohexyl-3,4-difluorobenzene 20%

4-(2-(4-pentylcycloyhexyl)ethyl)cyclohexyl-3,4-difluorobenzene 40% was prepared.

Liquid crystal composition (D) was prepared by mixing 10% by weight of 2-(4-(3-fluoro-4-trifluoromethoxyphenyl)-3,5-difluorophenyl)-5-pentylpyrimidine (Compound No. 17) with 90% by weight of the liquid crystal composition (C) described above. Voltage holding ratio of the liquid crystal composition (D) was 97.5% at 25° C. and 93.2% at 100° C.

Example 5 (Comparative Example 2)

Liquid crystal composition (D-R) comprising 90% by weight of the liquid crystal composition (C) described above and 10% by weight of 2-(4-(3,4,5-trifluorophenyl)phenyl)-5-pentylpyrimidine (compound of the formula 10) was prepared. Voltage holding ratio of the liquid crystal composition (D-R) was 97.5% at 25° C. and 92.9% at 100° C.

Accordingly, it can be seen that voltage holding ratio of the compound of the present invention (Compound No. 17) is by no means inferior to known pyrimidine derivative (compound of the formula 10).

Example 6

Liquid crystal composition (D2) comprising 95% by weight of the liquid crystal composition (C) described above and 5% by weight of 2-(4-(3-fluoro-4-trifluorormethoxyphenyl)-3,5-difluorophenyl)-5-pentylpyrimidine (Compound No. 17) was prepared. This liquid crystal composition exhibited nematic phase even after it was left at −20° C. for 30 days.

Example 7 (Comparative Example 3)

Liquid crystal composition (D2-R) comprising 95% by weight of the liquid crystal composition (C) described above and 5% by weight of 2-(4-(3,4,5-trifluorophenyl)phenyl)-5-pentylpyrimidine (compound of the formula 10) was prepared. This liquid crystal composition separated crystals when it was left at −20° C. for 30 days.

Accordingly, it can be seen that miscibility of the compound of the present invention (Compound No. 17) with other fluorine substituted liquid crystal compounds is more excellent than that of known compound of the formula (10).

Any compounds of the present invention are characterized by having a high Δε, high Δn, and comparatively high voltage holding ratio, and being excellent in miscibility with other liquid crystalline compounds at low temperatures. By using the compounds of the present invention as component of liquid crystal compositions, production of TFT type liquid crystal display devices having a still smaller becomes possible.

What is claimed is:

1. A pyrimidine derivative expressed by the general formula (1)

$$R-(A)_{n1}-Za-\text{[pyrimidine]}-Zb-(B)_{n2}-Zc-\text{[phenyl with }Q_4, Q_5, Q_6, Q_7\text{]}-Y \tag{1}$$

wherein R represents hydrogen atom or an alkyl group having 1 to 20 carbon atoms, at least one hydrogen atom in the alkyl group may be replaced by a halogen atom, and at least one —CH$_2$— in the alkyl group may be replaced by oxygen atom or —CH=CH— but in no case oxygen atoms adjoin to each other;

n1 and n2 are independently 0, 1, or 2 provided that the sum of n1 and n2 is 1 or 2, ring A and ring B independently represent 1,4-phenylene, fluorine substituted 1,4-phenylene expressed by the formula (a)

(a)

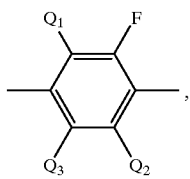

or 1,4-cyclohexylene provided that at least one of ring A and ring B is fluorine substituted 1,4-phenylene expressed by the formula (a), and that when ring A and/or ring B is the fluorine substituted 1,4-phenylene, then n1 and/or n2 is 1 or 2, at least one not-adjacent —$CH_2$— in the 1,4-cyclohexylene may be replaced by oxygen atom, and at least one hydrogen atom in the 1,4-cyclohexylene may be replaced by a halogen atom; Za, Zb, and Zc independently represent single bond, —$CH_2CH_2$—, —COO—, —$CF_2$—, or —$CH_2CH_2CH_2CH_2$—;

$Q_1$, $Q_2$, $Q_3$ $Q_4$ $Q_5$, $Q_6$, and $Q_7$ independently represent hydrogen atom, a halogen atom, or methyl group provided that when at least one of Za, Zb, and Zc is —$CH_2CH_2$—, then $Q_2$ is fluorine atom, that when any one of Za, Zb, and Zc is —COO—, then $Q_1$, $Q_2$, $Q_3$, $Q_4$, $Q_5$, $Q_6$, and $Q_7$ independently represent hydrogen atom, fluorine atom, or methyl group, and that when Za, Zb, and Zc are all single bonds, then $Q_1$, $Q_2$, $Q_3$, $Q_4$, $Q_5$, $Q_6$, and $Q_7$ independently represent hydrogen atom or fluorine atom;

Y represents a halogen atom, or a halogenated straight chain alkyl group having 1 to 5 carbon atoms, at least one not-adjacent methylene group in the halogenated alkyl group may be replaced by oxygen atom or sulfur atom, provided that when the halogenated alkyl group has two carbon atoms, then in no case are all hydrogen atoms in the halogenated alkyl group replaced by fluorine atoms, and that when the halogenated alkyl group has 3 to 5 carbon atoms, then a not-adjacent methylene group is replaced by oxygen atom or sulfur atom; and each atom constituting this compound may be replaced by its isotope.

2. The pyrimidine derivative according to claim 1 wherein n1 is 0, n2 is 1, all of Za, Zb, and Zc are single bond, both of $Q_1$ and $Q_3$ are hydrogen atom, and $Q_2$ is fluorine atom in the general formula (1).

3. The pyrimidine derivative according to claim 1 wherein n1 is 0, n2 is 1, all of Za, Zb, and Zc are single bond, and all of $Q_1$, $Q_2$, and $Q_3$ are hydrogen atom in the general formula (1).

4. The pyrimidine derivative according to claim 1 wherein n1 is 1 and n2 is 0 in the general formula (1).

5. The pyrimidine derivative according to claim 1 wherein n1 is 0, n2 is 1, both Za and Zb are single bond, and Zc is —COO— or —$CF_2O$— in the general formula (1).

6. The pyrimidine derivative according to claim 1 wherein n1 is 0, n2 is 1, both Za and Zc are single bond, and Zb is —COO— or —$CF_2O$— in the general formula (1).

7. The pyrimidine derivative according to claim 1 wherein n1+n2=2 in the general formula (1).

8. The pyrimidine derivative according to claim 1 wherein R is an alkyl group at least one hydrogen atom in which is replaced by fluorine atom in the general formula (1).

9. A liquid crystal composition comprising at least one pyrimidine derivative defined in any one of claims 1 to 8.

10. A liquid crystal composition comprising, as a first component, at least one pyrimidine derivative defined in any one of claims 1 to 8, and comprising, as a second component, at least one compound selected from the group consisting of the compounds expressed by the general formula (2), (3), or (4)

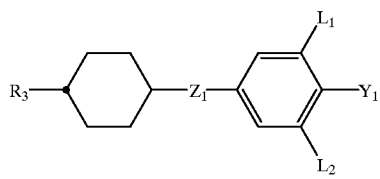

(2)

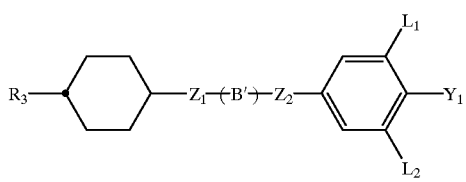

(3)

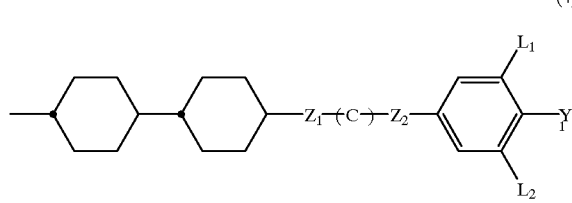

(4)

wherein $R_3$, $Y_1$, $L_1$, $L_2$, $Z_1$, and $Z_2$ may be the same or different among the formulas, $R_3$ represents an alkyl group having 1 to 10 carbon atoms, at least one not-adjacent methylene group in the alkyl group may be replaced by oxygen atom or —CH=CH—, and any hydrogen atom in the alkyl group may be replaced by fluorine atom; $Y_1$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$; $L_1$ and $L_2$ independently represent hydrogen atom or fluorine. atom; $Z_1$ and $Z_2$ independently represent —$CH_2CH_2$—, —$CH_2CH_2CH_2CH_2$—, —COO—, —$CF_2O$—, —$OCF_2$—, —CH=CH—, or single bond; ring B' represents trans-1,4-cyclohexylene, 1,3-dioxane-2,5-diyl, or 1,4-phenylene of which one or more hydrogen atom may be replaced by fluorine atom; ring C represents trans-1,4-cyclohexylene or 1,4-phenylene of which one or more hydrogen atom may be replaced by fluorine atom; and each atom constituting this compound may be replaced by its isotope.

11. A liquid crystal composition comprising, as a first component, at least one pyrimidine derivative defined in any one of claims 1 to 8, and comprising, as a second component, at least one compound selected from the group consisting of the compounds expressed by the general formula (5) or (6)

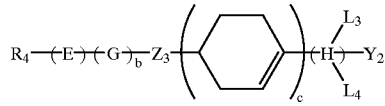

(5)

(6)

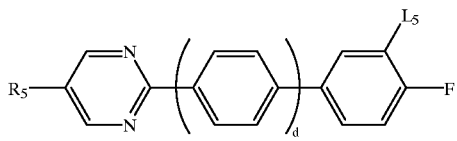

wherein $R_4$ and $R_5$ independently represent an alkyl group having 1 to 10 carbon atoms, at least one not-adjacent methylene group in the alkyl group may be replaced by oxygen atom or —CH=CH—, and hydrogen atom in the alkyl group may be replaced by fluorine atom; $Y_2$ represents —CN or —C≡C—CN; ring E represents trans-1,4-cyclohexylene, 1,4-phenylene, 1,3-dioxane-2,5-diyl, or pyrimidine-2,5-diyl; ring G represents trans-1,4-cyclohexylene, pyrimidine-2,5-diyl, or 1,4-phenylene of which one or more hydrogen atom may be replaced by fluorine atom; ring H represents trans-1,4-cyclohexylene or 1,4-phenylene, $Z_3$ represents —CH$_2$CH$_2$—, —COO—, or single bond; $L_3$, $L_4$, and $L_5$ independently represent hydrogen atom or fluorine atom; b, c, and d are independently 0 or 1; and each atom constituting this compound may be replaced by its isotope.

12. A liquid crystal composition comprising, as a first component, at least one pyrimidine derivative defined in any one of claims 1 to 8, comprising, as a second component, at least one compound selected from the group consisting of the compounds expressed by the general formula (2), (3), or (4)

(2)

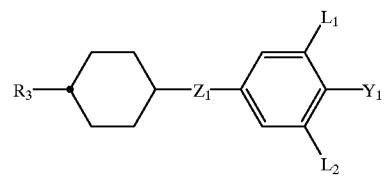

(3)

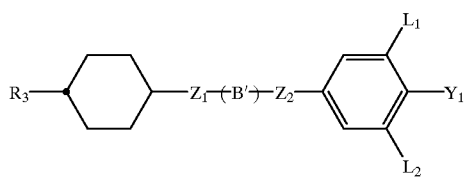

(4)

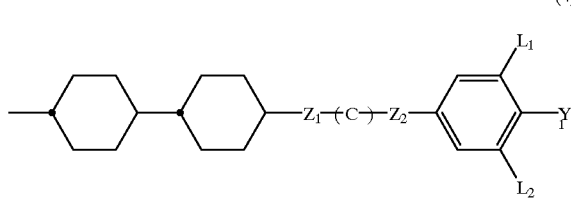

wherein $R_3$, $Y_1$, $L_1$, $L_2$, $Z_1$, and $Z_2$, may be the same or different among the formulas, $R_3$ represents an alkyl group having 1 to 10 carbon atoms, at least one not-adjacent methylene group in the alky group may be replaced by oxygen atom or —CH=CH—, and any hydrogen atom in the alkyl group may be replaced by fluorine atom; $Y_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently represent hydrogen atom or fluorine atom; $Z_1$ and $Z_2$ independently represent —CH$_2$CH$_2$—, —CH$_2$CH$_2$CH$_2$CH$_2$—, —COO—, CF$_2$O—, OCF$_2$—, —CH=CH—, or single bond; rind B' represents trans-1,4-cyclohexnlene, 1,3-dioxane-2,5-diyl, or 1,4-phenylene of which one or more hydrogen atom may be replaced by fluorine atom; ring C represents trans-1,4-cyclohexylene or 1,4-phenylene of which one or more hydrogen atom may be replaced by fluorine atom; and each atom constituting this compound may be replaced by its isotope, and comprising, as a third component, at least one compound selected from the group consisting of the compounds expressed by the general formula (7), (8), or (9)

(7)

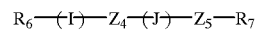

(8)

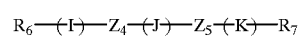

(9)

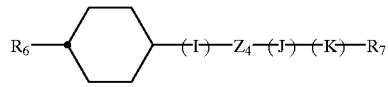

wherein $R_6$, $R_7$, I, J, and K may be the same or different among the general formulas, $R_6$ and $R_7$ independently represent an alkyl group having 1 to 10 carbon atoms, at least one methylene group in the alkyl group may be replaced by oxygen atom or —CH=CH—, and any hydrogen atom in the alkyl group may be replaced by fluorine atom; ring I, ring J, and ring K independently represent trans-1,4-cyclohexylene, pyrimidine-2,5-diyl, or 1,4-phenylene of which one or more hydrogen atom may be replaced by fluorine atom; $Z_4$ and $Z_5$ independently represent —C≡C—, —COO—, —CH$_2$CH$_2$—, —CH=CH—, or single bond; and each atom constituting this compound may be replaced by its isotope.

13. A liquid crystal composition comprising, as a first component, at least one pyrimidine derivative defined in any one of claims 1 to 8, comprising, as a second component, at least one compound selected from the group consisting of the compounds expressed by the general formula (5) or (6)

(5)

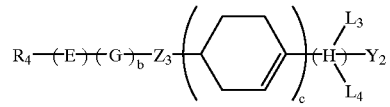

(6)

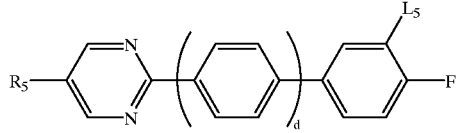

wherein $R_4$ and $R_5$ independently represent an alkyl group having 1 to 10 carbon atoms, at least one not-adiacent methylene group in the alkyl group may be replaced by oxygen atom or —CH=CH—, and any hydrogen atom in the alkyl group may be replaced by fluorine atom; $Y_2$ represents —CN or —C≡C—CN; ring E represents trans-1,4-cyclohexlene, 1,4-phenylene, 1,3-dioxane-2,5-diyl, or pyrimidine-2,5-diyl; ring G represents trans-1,4-cyclohexylene, pyrimidine-2, 5-diyl, or 1,4-phenylene of which one or more hydrogen atom may be replaced by fluorine atom; ring H represents trans-1,4-cyclohexylene or 1,4-phenylene, $Z_3$ represents —CH$_2$CH$_2$—, —COO—, or single bond; $L_3$, $L_4$ and $L_5$ independently represent hydrogen atom or fluorine atom; b, c, and d are independently 0 or 1; and each atom constituting this compound may be replaced by its isotope, and comprising, as a third compound, at least one compound selected from the group consisting of the compounds expressed by the general formula (7), (8), or (9)

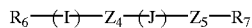
(7)

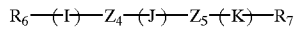
(8)

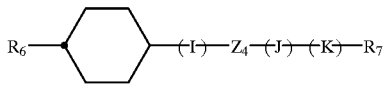
(9)

wherein $R_6$, $R_7$, I, J, and K may be the same or different among the general formulas, $R_6$ and $R_7$ independently represent an alkyl group having 1 to 10 carbon atoms, at least one methylene group in the alkyl group may be replaced by oxygen atom or —CH═CH—, and any hydrogen atom in the alkyl group may be replaced by fluorine atom; ring I, ring J, and ring K independently represent trans-1,4-cyclohexylene, pyrimidine-2,5-diyl, or 1,4-phenylene of which one or more hydrogen atom may be replaced by fluorine atom; $Z_4$ and $Z_5$ independently represent —C≡C—, —COO—, —CH$_2$CH$_2$—, —CH═CH—, or single bond; and each atom constituting this compound may be replaced by its isotope.

14. A liquid crystal composition comprising, as a first component, at least one pyrimidine derivative defined in one of claims 1 to 8, comprising, as a part of a second component, at least one compound selected from the group consisting of the compounds expressed by the general formula (2), (3), or (4)

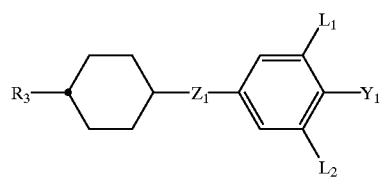
(2)

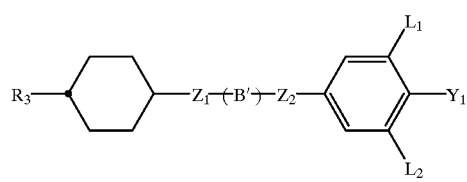
(3)

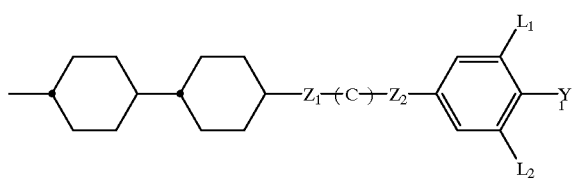
(4)

wherein $R_3$, $Y_1$, $L_1$, $L_2$, $Z_1$, and $Z_2$, may be the same or different among the formulas, R, represents an alkyl group having 1 to 10 carbon atoms, at least one not-adiacent methylene group in the alkyl group may be replaced by oxygen atom or —CH═CH—, and any hydrogen atom in the alkyl group may be replaced by fluorine atom; $Y_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$, $L_1$ and $L_2$ independently represent hydrogen atom or fluorine atom; $Z_1$ and $Z_2$ independently represent —CH$_2$CH$_2$—, —CH$_2$CH$_2$CH$_2$CH$_2$—, —COO—, CF$_2$O—, OCF$_2$—, —CH═CH—, or single bond; ring B' represents trans-1,4-cyclohexylene, 1,3-dioxane-2,5-diyl, or 1,4-phenylene of which one or more hydrogen atom may be replaced by fluorine atom; ring C represents trans-1,4-cyclohexylene or 1,4-phenylene of which one or more hydrogen atom may be replaced by fluorine atom; and each atom constituting this compound may be replaced by its isotope, comprising, as another part of the second component, at least one compound selected from the group consisting of the compounds expressed by the general formula (5) or (6)

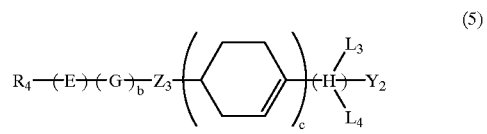
(5)

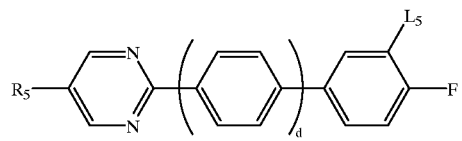
(6)

wherein $R_4$ and $R_5$ independently represent an alkyl group having 1 to 10 carbon atoms, at least one not-adiacent methylene group in the alkyl group may be replaced by oxygen atom or —CH═CH—, and any hydrogen atom in the alkyl group may be replaced by fluorine atom; $Y_2$ represents —CN or —C≡C—CN; ring E represents trans-1,4-cyclohexylene, 1,4-phenylene, 1,3-dioxane-2,5-diyl, or pyrimidine-2,5-diyl; ring G represents trans-1,4-cyclohexylene, pyrimidine-2,5-diyl, or 1,4-phenylene of which one or more hydrogen atom may be replaced by fluorine atom; ring H represents trans-1,4-cyclohexylene or 1,4-phenylene, $Z_3$ represents —CH$_2$CH$_2$—, —COO—, or single bond; $L_3$, $L_4$ and $L_5$ independently represent hydrogen atom or fluorine atom; b, c, and d are independently 0 or 1; and each atom constituting this compound may be replaced by its isotope, and comprising, as a third component, at least one compound selected from the group consisting of the compounds expressed by the general formula (7), (8), or (9)

(7)

(8)

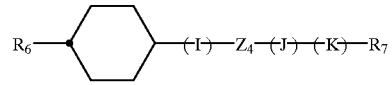
(9)

wherein $R_6$, $R_7$, I, J, and K may be the same or different among the general formulas, $R_6$ and $R_7$ independently represent an alkyl group having 1 to 10 carbon atoms, at least one methylene group in the alkyl group may be replaced by oxygen atom or —CH═CH—, and any hydrogen atom in the alkyl group may be replaced by fluorine atom; ring I, ring J, and ring K independently represent trans-1,4-cyclohexylene, pyrimidine-2,5-diyl, or 1,4-phenylene of which one or more hydrogen atom may be replaced by fluorine atom; $Z_4$ and $Z_5$ independently represent —C≡C—, —COO—, —CH$_2$CH$_2$—, —CH=CH—, or single bond; and each atom constituting this compound may be replaced by its isotope.

15. A liquid crystal composition comprising the liquid crystal composition defined in claim 9 and further comprising at least one optically active compound.

16. A liquid crystal composition comprising the liquid crystal composition defined in claim 10 and further comprising at least one optically active compound.

17. A liquid crystal composition comprising the liquid crystal composition defined in claim 11 and further comprising at least one optically active compound.

18. A liquid crystal composition comprising the liquid crystal composition defined in claim 12 and further comprising at least one optically active compound.

19. A liquid crystal composition comprising the liquid crystal composition defined in claim 13 and further comprising at least one optically active compound.

20. A liquid crystal composition comprising the liquid crystal composition defined in claim 14 and further comprising at least one optically active compound.

21. A liquid crystal display device comprising the liquid crystal composition defined in claim 9.

22. A liquid crystal display device comprising the liquid crystal composition defined in claim 10.

23. A liquid crystal display device comprising the liquid crystal composition defined in claim 11.

24. A liquid crystal display device comprising the liquid crystal composition defined in claim 12.

25. A liquid crystal display device comprising the liquid crystal composition defined in claim 13.

26. A liquid crystal display device comprising the liquid crystal composition defined in claim 14.

27. A liquid crystal display device comprising the liquid crystal composition defined in claim 15.

28. A liquid crystal display device comprising the liquid crystal composition defined in claim 16.

29. A liquid crystal display device comprising the liquid crystal composition defined in claim 17.

30. A liquid crystal display device comprising the liquid crystal composition defined in claim 18.

31. A liquid crystal display device comprising the liquid crystal composition defined in claim 19.

32. A liquid crystal display device comprising the liquid crystal composition defined in claim 20.

* * * * *